US011965831B2

(12) United States Patent
Gopinath et al.

(10) Patent No.: US 11,965,831 B2
(45) Date of Patent: Apr. 23, 2024

(54) METHODS AND SYSTEMS FOR STIMULATED EMISSION DEPLETION MICROSCOPY

(71) Applicant: THE REGENTS OF THE UNIVERSITY OF COLORADO, A BODY CORPORATE, Denver, CO (US)

(72) Inventors: Juliet T. Gopinath, Boulder, CO (US); Brendan M. Heffernan, Boulder, CO (US); Robert Niederriter, Los Angeles, CA (US); Stephanie A. Meyer, Denver, CO (US); Diego Restrepo, Littleton, CO (US); Emily A. Gibson, Boulder, CO (US); Mark E. Siemens, Denver, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 16/976,946

(22) PCT Filed: Mar. 1, 2019

(86) PCT No.: PCT/US2019/020448
§ 371 (c)(1),
(2) Date: Aug. 31, 2020

(87) PCT Pub. No.: WO2019/169368
PCT Pub. Date: Sep. 6, 2019

(65) Prior Publication Data
US 2021/0372927 A1   Dec. 2, 2021

Related U.S. Application Data

(60) Provisional application No. 62/639,438, filed on Mar. 6, 2018, provisional application No. 62/637,375, filed on Mar. 1, 2018.

(51) Int. Cl.
*G01N 21/64* (2006.01)
*G02B 3/00* (2006.01)
(Continued)

(52) U.S. Cl.
CPC ....... *G01N 21/6458* (2013.01); *G02B 3/0087* (2013.01); *G02B 21/0032* (2013.01);
(Continued)

(58) Field of Classification Search
CPC ....... G01N 21/6458; G01N 2021/6484; G01N 21/6445; G01N 2021/6419; G02B 3/0087;
(Continued)

(56) References Cited

U.S. PATENT DOCUMENTS

2009/0028332 A1   1/2009  Parker
2012/0287244 A1*  11/2012 Bennett ............... H01J 37/228
                                          348/46
(Continued)

FOREIGN PATENT DOCUMENTS

JP   2004-064513 A   2/2004
JP   2010-199308 A   9/2010
(Continued)

OTHER PUBLICATIONS

Rakhi et al. "Optical Vortex in Photonic Crystal Fiber by Finite Element Method", The International Conference on Fiber Optics and Photonics, 2016, p. 1-3 (Year: 2016).*
(Continued)

*Primary Examiner* — David P Porta
*Assistant Examiner* — Mamadou Faye
(74) *Attorney, Agent, or Firm* — McDonnell Boehnen Hulbert & Berghoff LLP

(57) ABSTRACT

Sub-diffraction limited fluorescent images using a fiber-based stimulated emission depletion (STED) microscope are reported. Both excitation and depletion beams are trans-
(Continued)

ported through polarization-maintaining fiber and a lateral resolution of 100 nm has been achieved.

20 Claims, 11 Drawing Sheets

(51) Int. Cl.
　　*G02B 21/00*　　　(2006.01)
　　*G02B 27/58*　　　(2006.01)
(52) U.S. Cl.
　　CPC ..... *G02B 21/0068* (2013.01); *G02B 21/0076* (2013.01); *G02B 27/58* (2013.01); *G01N 2021/6484* (2013.01)
(58) Field of Classification Search
　　CPC ............ G02B 21/0032; G02B 21/0068; G02B 21/0076; G02B 27/58; A61B 1/00188; A61B 5/0068; A61B 2562/028; A61B 1/0017; A61B 1/043; A61B 1/0607; A61B 1/0638; A61B 1/0646; A61B 1/07; A61B 5/0071
　　See application file for complete search history.

(56) References Cited

U.S. PATENT DOCUMENTS

| 2015/0015879 | A1 | 1/2015 | Papadopoulos et al. |
| 2017/0336326 | A1 | 11/2017 | Sirat |

FOREIGN PATENT DOCUMENTS

| WO | 2017/210679 | 12/2017 | |
| WO | WO-2017210679 A1 * | 12/2017 | ............ A61B 1/0017 |

OTHER PUBLICATIONS

The International Search Report (ISR) with Written Opinion for PCT/US2019/020448 dated May 10, 2019, pp. 1-8.
Daendliker, Rene "Concept of modes in optics and photonics" Proceedings SPIE Sixth International Conference on Education and Training in Optics and Photonics (2000) vol. 3831, pp. 193-198.
Yan, L. et al. "Q-piate enabled spectrally diverse orbital-angular-momentum conversion for stimulated emission depletion microscopy." Optica (2015) vol. 2(10), pp. 900-903.
S.W. Hell and J. Wichmann, "Breaking the diffraction resolution limit by stimulated emission: stimulated-emission-depletion fluorescence microscopy," Optics Letters, 19(11), 780-782 (1994).
B. Neupane et al., "Tuning donut profile for spatial resolution in stimulated emission depletion microscopy," Review of Scientific Instruments, 84, 043701-1-043701-9 (2013).
S. Ramachandran and P. Kristensen "Optical vortices in fiber," Nanophotonics, 2(5-6), 455-474 (2013).
J.N. Farahani, "Stimulated Emission Depletion (STED) Microscopy: from Theory to Practice," in Microscopy: Science, Technology, Applications and Education, A. Mendez-Vilas and J. Diaz, Eds, pp. 1539-1547, copyright Formatex (2010).
H. Blom and J. Widengren, "Stimulated Emission Depletion Microscopy," Chem. Rev., 117, 7377-7427 (2017).
C. Eggeling et al., "Direct Observation of the nanoscale dynamics of membrane lipids in a living cell," Nature, 457, 1159-1163 (2009).
T. Pfeiffer et al., "Chronic 2P-STED imaging reveals high turnover of dendritic spines in the hippocampus in vivo," eLife, 7:e34700, pp. 1-17 (2018).
C. Eggeling et al., "STED microscopy of living cells—new frontiers in membrane and neurobiology," J. Neurochemistry, 126, 203-212 (2013).
N. Bokor, "Investigation of polarization effects for high-numerical-aperture first-order Laguerre-Gaussian beams by 2D scanning with a single fluorescent microbead," Optics Express, 13(26), 10440-47 (2005).
B. Harke, "Resolution scaling in STED microscopy," Optics Express, 16(6), 4154-62 (2008).
M. Vitek and I. Musevic, "Nanosecond control and optical pulse shaping by stimulated emission depletion in a liquid crystal," Optics Express, 23(13), 16921-32 (2015).
R.D. Niederriter et al., "Continuously tunable orbital angular momentum generation using a polarization-maintaining fiber," Optics Letters, 41(14), 3213-16 (2016).
B.M. Heffernan et al., "Tunable higher-order angular momentum using polarization-maintaining fiber," Optics Letters, 42(14), 2583-86 (2017).
T.A. Klar et al., "Breaking Abbe's diffraction resolution limit in fluorescence microscopy with stimulated emission depletion beams of various shapes," Phys. Rev. E., 64, 066613-1-066613-9 (2001).
J. Tonnensen et al., "Two-Color STED Microscopy of Living Synapses Using a Single Laser-Beam Pair," Biophysical Journal, 101, 2545-52 (2011).
B. Hein et al., "Stimulated emission depletion (STED) nanoscopy of a fluorescent protein-labeled organelle inside a living cell," Proceedings of the National Academy of Sciences, 105(38), 14271-76 (2008).
W. Wegner et al., "In vivo STED microscopy visualizes PSD95 sub-structures and morphological changes over several hours in the mouse visual cortex," Scientific Reports, 8:219, 1-11 (2018).
V. Westphal et al., "Video-Rate Far-Field Optical Nanoscopy Dissects Synaptic Vessicle Movement," Science, 320, 246-249 (2008).
S. Berning et al., "Nanoscopy in a Living Mouse Brain," Science, 335, 551 (2012).
V. Westphal et al., "Dynamic far-field fluorescence nanoscopy," New J. Phys., 9, 435 (2007).

* cited by examiner

METHODS AND SYSTEMS FOR STIMULATED EMISSION DEPLETION MICROSCOPY

CROSS-REFERENCE TO RELATED APPLICATIONS

This application is a U.S. National Stage application of International Patent Application no. PCT/US2019/020448, which claims the benefit of priority of U.S. Provisional Patent Application No. 62/637,375, filed Mar. 1, 2018, and U.S. Provisional Patent Application No. 62/639,438, filed Mar. 7, 2018, each of which is hereby incorporated by reference herein in its entirety.

STATEMENT OF GOVERNMENT SUPPORT

This invention was made with government support under grant numbers 1509928, 1353757 and 1337573, awarded by the National Science Foundation. The government has certain rights in the invention.

BACKGROUND OF THE DISCLOSURE

1. Field of the Disclosure

The present disclosure relates generally to systems and methods for microscopy, and particularly to methods and systems for stimulated emission depletion microscopy.

2. Technical Background

Stimulated emission depletion (STED) microscopy is an important technique that can overcome the diffraction limit and resolve structures on the order of ~40 nm. It is a powerful method that is particularly useful in a biological setting with fluorophores, where it can be used to monitor subcellular activity in situ. Typical STED setups rely on two laser beams at different wavelengths: a Gaussian excitation beam overlapped with a "donut" depletion beam. The depletion beam (also called a STED beam) drives a process of stimulated emission that suppresses fluorescence everywhere except in the null at the center of the beam. The result is a region of fluorescent emission that is smaller than the diffraction limit. Laguerre-Gaussian (LG) beams with optical orbital angular momentum (OAM) offer a convenient donut mode, and so are frequently used as STED beams.

The applicability of STED can be enhanced by moving from free space to fiber optics, opening up the possibility for endoscopic and in vivo sub-diffraction limited imaging. The primary obstacle to fiber-based STED is that standard, commercially available step index fiber does not support OAM modes as eigenmodes. Significant progress has recently been made on a fiber-based STED microscope system using specialty vortex fibers, resulting in fluorescent spot sizes of 103 nm. See, e.g., Lu Yan et al., "All-fiber STED microscopy illumination system," CLEO 2016, SM4P. 3 (2016).

However, the present inventors have noted that beams with OAM have been produced using polarization maintaining fiber by coupling to orthogonal Hermite-Gaussian-like linear-polarized modes, but dependence on the relative phase of the modes at the fiber output make the system highly sensitive to perturbation and bending of the fiber.

Accordingly, what are needed are improved methods and systems for STED microscopy.

SUMMARY OF THE DISCLOSURE

One aspect of the disclosure is a method for stimulated emission depletion microscopy of a fluorescent species in an object to be imaged, the fluorescent species having a fluorescence excitation wavelength, a fluorescence depletion wavelength and an fluorescence emission wavelength, the method comprising:

providing a polarization-maintaining optical fiber;

propagating excitation radiation of the fluorescence excitation wavelength in a central mode of the fiber;

propagating depletion radiation of the fluorescence depletion wavelength in one or more peripheral modes of the fiber, each of the one or more peripheral modes having a minimum of intensity substantially overlapping the central mode of the fiber, the depletion radiation propagating substantially temporally incoherently in the fiber;

delivering the excitation radiation and the depletion radiation from the optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the spot, wherein the excitation radiation causes emission radiation of the fluorescence emission wavelength from the object at the centrally-disposed intensity maximum of the spot, and the depletion radiation prevents emission of radiation of the fluorescence emission wavelength in the region of the annular depletion radiation; and determining the intensity of the emission radiation.

Another aspect of the disclosure is an optical system configured to perform the methods as described herein. For example, in certain embodiments, such an optical system includes a polarization-maintaining optical fiber having a central mode and one or more peripheral modes each having a minimum of intensity substantially overlapping the central mode of the polarization-maintaining optical fiber;

a source of excitation radiation and coupled to cause propagation of excitation radiation of the fluorescence excitation wavelength in the central mode of the polarization-maintaining optical fiber;

a source of depletion radiation coupled to cause propagation of depletion radiation substantially temporally incoherently in one or more of the peripheral modes of the fiber;

the polarization-maintaining optical fiber being configured to deliver the excitation radiation and the depletion radiation from the optical fiber to the object to be imaged (e.g., optionally through additional optics), with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the spot, wherein the excitation radiation causes emission radiation of the fluorescence emission wavelength from the object at the centrally-disposed intensity maximum of the spot, and the depletion radiation prevents emission of radiation of the fluorescence emission wavelength in the region of the annular depletion radiation.

Additional aspects of the disclosure will be evident from the disclosure herein.

BRIEF DESCRIPTION OF THE DRAWINGS

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more embodiment(s) of the disclosure and together with the description serve to explain the principles and operation of the disclosure.

DETAILED DESCRIPTION

Figure 1:
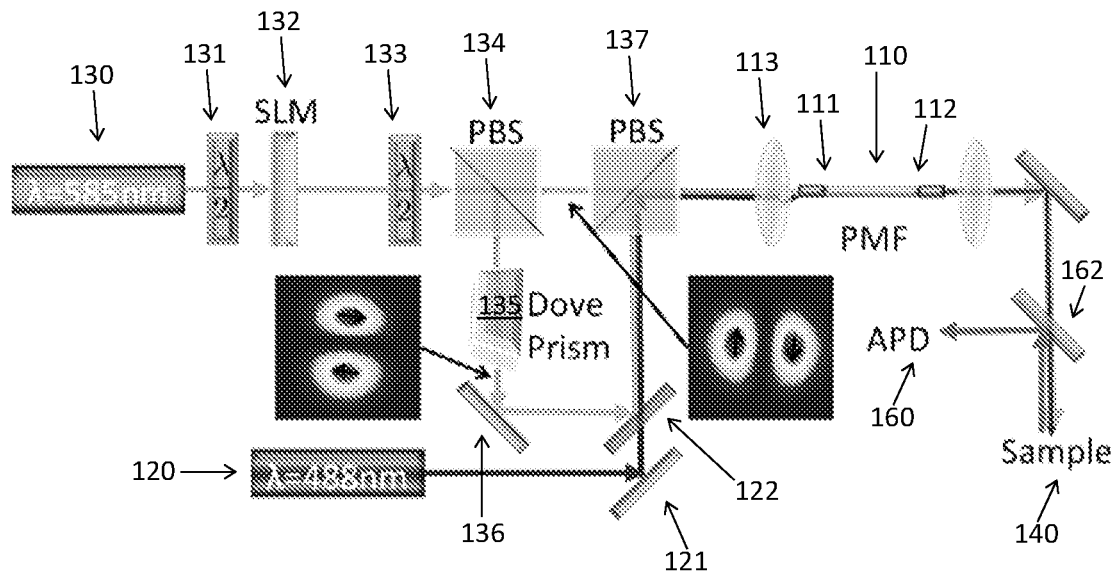
FIG. 1 provides a schematic view of a fiber-based STED system according to the disclosure. SLM—spatial light modulator. PBS—polarizing cube beam splitter. PMF—polarization-maintaining fiber. APD—avalanche photodiode. Diagram of the fiber-based STED system. The depletion laser is shaped into a Hermite-Gaussian-like mode by the SLM to efficiently couple to the higher-order fiber eigenmodes. It is then split into two arms and a Dove prism in one rotates the beam profile (insets, in each of which the dark portions in the two lobes represent intensity maxima, and the dark portions outside the loves represent intensity minima). The excitation laser is passed in through a high-pass dichroic mirror, and both excitation and STED beams are coupled into polarization-maintaining fiber. The light from fiber can then be sent to image a sample with the fluorescence collected and detected using an APD.

The present inventors have determined a number of improvements in optical fiber-based STED microscopy. For example, the present inventors have determined that if the two orthogonal linear-polarized modes (e.g., orthogonal Hermite-Gaussian-like linear-polarized modes) are temporally incoherent, an annular (or "donut-shaped") beam with no substantial dependence on relative phase can be realized and hence is substantially insensitive to fiber conditions such as physical perturbations of the optical fiber. The present inventors have determined that use of such temporally-incoherent linearly-polarized modes can provide significant improvements in methods and optical systems for fiber-based STED microscopy, as described herein.

STED imaging uses two laser beams at different wavelengths: an excitation beam (e.g., Gaussian) overlapped with a "donut"-shaped depletion beam, typically at a longer wavelength. The depletion beam (STED beam) drives a process of stimulated emission that suppresses fluorescence everywhere except in the null at the center of the depletion beam. The result is a region of fluorescent emission that is smaller than the diffraction limit, with the STED beam inhibiting fluorescence at the periphery of the excitation beam, providing an effectively smaller pixel size to an image. Laguerre-Gaussian (LG) beams with optical orbital angular momentum (OAM) offer a convenient donut mode, and so are frequently used as STED depletion beams. The appeal of the OAM beams is that the helical phase structure and inherent phase singularity leads to a very dark null in the center of the beam (>13 dB contrast relative to rest of beam). This dark null is highly desirable for a STED beam, because resolution can be degraded without it. However, it is important to note that it is not necessary for a STED beam to have substantial OAM; more generally, any donut-shaped beam with good contrast (e.g., at least 10 dB, or even at least 13 dB) between the dark center of the beam and the intense outer portions will be a desirable depletion beam in STED. And in certain embodiments of the methods and systems as otherwise described herein, the depletion radiation does not have substantial OAM.

Accordingly, one aspect of the disclosure is an optical system for STED microscopy of a fluorescent species in an object to be imaged. One example of such an optical system is shown in schematic view in FIG. 1. Optical system 100 of FIG. 1 includes a polarization-maintaining optical fiber 110 having a central mode and one or more (e.g., at least two) peripheral modes each having a minimum of intensity substantially overlapping the central mode of the polarization-maintaining optical fiber. Optical system 100 also includes a source of excitation radiation 120 of a fluorescence excitation wavelength, and a source of depletion radiation 130 of a fluorescence depletion wavelength. The source of excitation radiation 120 is coupled to cause propagation of excitation radiation of the in the central mode of the polarization-maintaining optical fiber 110, for example, from a first end 111 to a second end 112 thereof. The source of depletion radiation is coupled to cause propagation of depletion radiation in one or more (e.g., at least two, or two) of the peripheral modes of the polarization-maintaining optical fiber 110, for example, from a first end 111 to a second end 112 thereof. Notably, the system is configured such that the depletion radiation is propagated substantially temporally incoherently in one or more (e.g., at least two, or two) peripheral modes of the polarization-maintaining optical fiber. The polarization-maintaining optical fiber is configured to deliver the excitation radiation from the optical fiber to the object to be imaged 140, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot. This is shown in schematic view in FIG. 2, in which the excitation radiation spot 250 has a centrally-disposed intensity maximum 251 and the depletion radiation 255 forms an annular ring about the excitation radiation and substantially overlaps the periphery of the excitation radiation spot without substantially overlapping the centrally-disposed intensity maximum of the spot. In use, the excitation radiation causes emission radiation of the fluorescence emission wavelength from the object at the centrally-disposed intensity maximum of the spot, and the depletion radiation substantially prevents emission of radiation of the fluorescence emission wavelength in the region of the annular depletion radiation. As the person of ordinary skill in the art will appreciate, additional optics can be used throughout the system, for example, to provide the excitation radiation to the polarization-maintaining optical fiber, to shape and to provide the depletion radiation to the polarization-maintaining optical fiber, and to transmit the excitation and depletion radiation to the object to be imaged.

Figure 2:
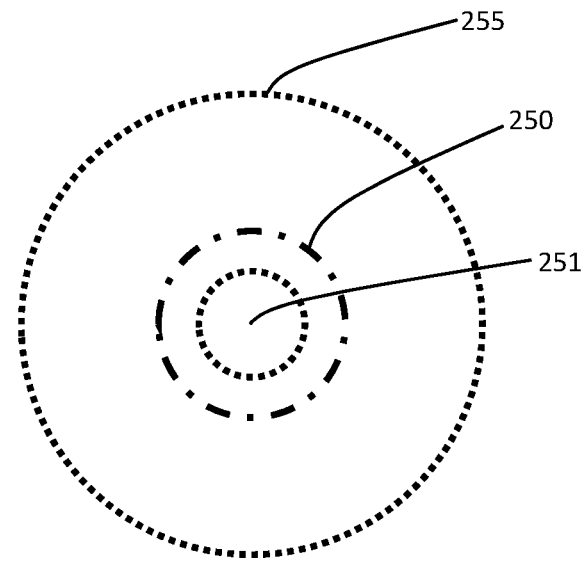
FIG. 2 is a diagram of overlapping excitation and depletion radiation.

In certain desirable embodiments, an optical system as otherwise described herein also includes an intensity detector configured to determine the intensity of the emission radiation from the object to be imaged. In the system of FIG. 1, detector 160 is configured to determine the intensity of radiation from the object to be imaged (here, by being reflected out of the primary beam path by dichroic mirror 162).

Another aspect of the disclosure is a method for stimulated emission depletion microscopy of a fluorescent species in an object to be imaged, the fluorescent species having a fluorescence excitation wavelength, a fluorescence depletion wavelength and an fluorescence emission wavelength. The methods can be performed, for example, using systems as described herein. But the person of ordinary skill in the art will appreciate that other systems can be adapted to perform the methods described herein. Such a method includes providing a polarization-maintaining optical fiber (e.g., 110 in FIG. 1); propagating excitation radiation of the fluorescence excitation wavelength in a central mode of the polarization-maintaining optical fiber (e.g., from first end 111 to second end 112 in FIG. 1); and propagating depletion radiation of the fluorescence depletion wavelength in one or more peripheral modes of the polarization-maintaining optical fiber (e.g., from first end 111 to second end 112 in FIG. 1), each of the one or more peripheral modes having a minimum of intensity substantially overlapping the central mode of the polarization-maintaining optical fiber (e.g., as described above with respect to FIG. 2), the depletion radiation propagating substantially temporally incoherently in the polarization-maintaining optical fiber. The method further includes delivering the excitation radiation and the depletion radiation from the polarization-maintaining optical fiber to the object to be imaged (140 in FIG. 1), with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot. The excitation radiation causes emission radiation of the fluorescence emission wavelength from the object at the centrally-disposed intensity maximum of the excitation radiation spot, and the depletion radiation prevents emission of radiation of the fluorescence emission wavelength in the region of the annular depletion radiation. The method further includes determining the intensity of the emission radiation (e.g., in the embodiment of FIG. 1, using dichroic mirror 162 and detector 160).

One particular embodiment of a method and system as described herein is shown in FIG. 1. In this embodiment 20 MHz, pulsed 488 nm light is used to excite green fluorescent proteins (GFP) in the object to be imaged, which are depleted using 585 nm light. Thus, the excitation wavelength is 488 nm and the depletion wavelength is 585 nm in this embodiment. The depletion light is supplied by depletion source 130 and is (after being passed through a half-wave plate 131) first incident on a spatial light modulator 132, which shapes the beam into a Hermite-Gaussian (HG) mode (e.g., a $TEM_{10}$ or a $TEM_{01}$ mode). It passes through a half-wave plate 133, and a first polarizing cube beam splitter 134 separates the beam into two arms of a Mach-Zehnder interferometer. In a first interferometer arm, a Dove prism 135 is used to rotate the spatial profile by 90° and delay the pulse. The excitation light is provided by excitation source 120. A dichroic mirror 122 reflects the depletion radiation in the first arm and is passes through the excitation radiation together into the beam path of the first interferometer arm. The dichroic mirror 122 is used to reflect the A second interferometer arm extends between first polarizing beam splitter 134 and a second polarizing beam splitter, which recombines the radiation in the two interferometer arms. The modes in the two interferometer arms are shown in FIG. 1; it is noted that they are similar but rotated 90 degrees from one another. The combined excitation and depletion radiation is coupled (e.g., using optic 113) into the polarization-maintaining optical fiber 110 that supports 6 modes (including polarization) at 585 nm and 12 modes at 488 nm. The fiber is loosely coiled on the table with a bend radius of approximately 50 mm. Care is taken to couple the excitation light (488 nm) into a Gaussian-like mode, which propagates without issue over the 2 m fiber length. No intermodal coupling is observed for modest bending radii of ~10 cm. In the embodiment of FIG. 1, a super achromatic, long working distance objective 114 is used to collimate the output of the fiber. The beam passes through a notch dichroic 162, and into an oil immersion, 100×, 1.4 NA microscope objective. A sample slide (i.e., bearing object 140) is placed on a high-precision, 3-axis piezo translation stage. As described above, the excitation radiation causes fluorescent emission from the object to be imaged. Fluorescence is collected back through the objective, split from the beam path using the notch dichroic 162, and focused into a multimode fiber with a core diameter of 62.5 μm that serves as a confocal pinhole. An avalanche photodiode at the end of the fiber provides sensitive detection (i.e., acting as the detector 160). Mirrors 136, 121 and 116 are used to conveniently route radiation in the system of FIG. 1, but the person of ordinary skill in the art will appreciate that in other implementations mirrors can be configured differently or even omitted entirely.

Of course, as the person of ordinary skill in the art will appreciate, the optical path can differ in other embodiments, however. For example, in certain embodiments, a GRIN lens-based optical can be used to minimize system size. And in certain embodiments, the fluorescence emission can be collected by the same polarization-maintaining fiber that delivers the excitation and depletion radiation. The person of ordinary skill in the art can use conventional techniques to minimize system size for use in portable instruments.

Figure 3:
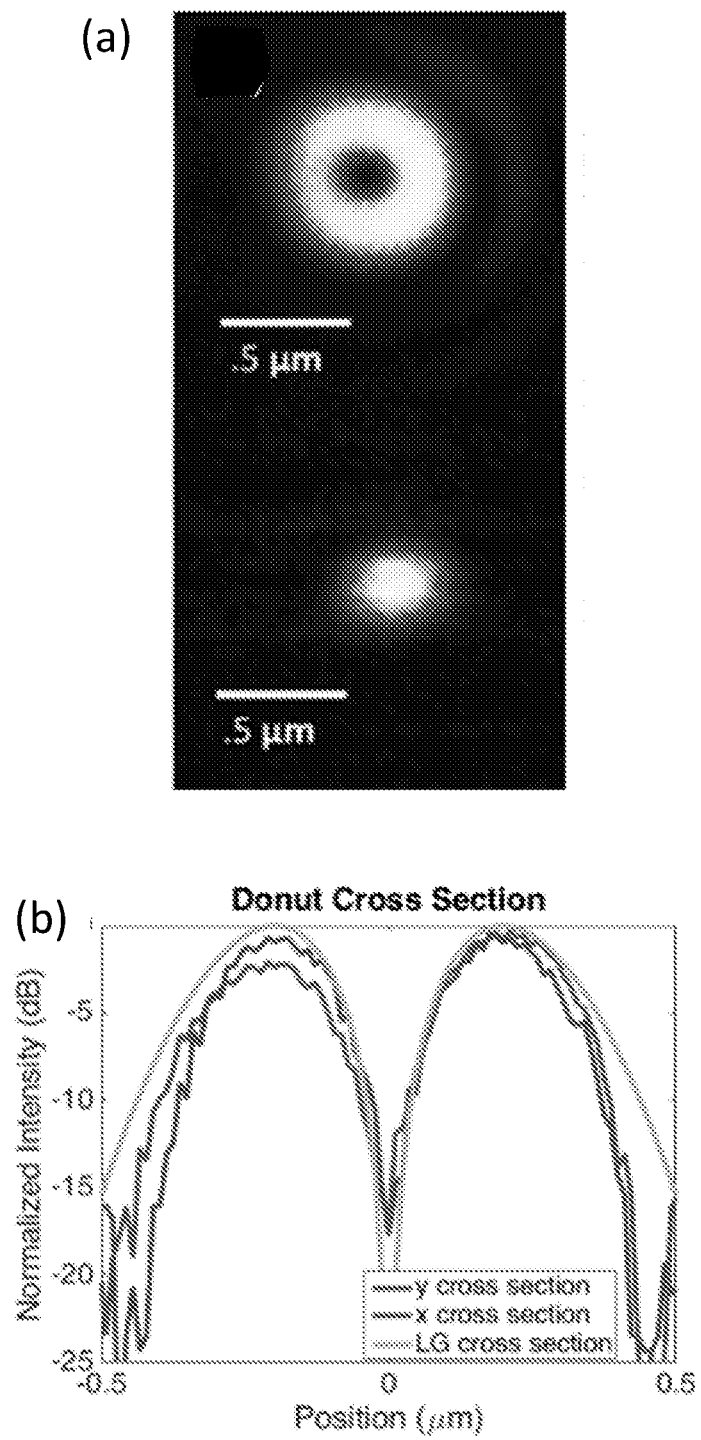
FIG. 3 provides in section (a) a demonstration of measured tight focusing of the STED (upper) and excitation (lower) beams using gold nanoparticles; and in section (b) Cross section of the STED beam showing better than 15 dB of intensity suppression compared to the peak of the donut.

To implement this technique in a STED microscope system, it can be important to take polarization effects into consideration. The paraxial approximation no longer holds in the high numerical aperture focusing conditions of STED microscopy, causing the polarization of the electric field vectors to 'tilt' into each other. Simulations of tight focusing using the Debye-Wolf integral show that an HG mode desirably has a polarization parallel to the dark nodal line of the beam in order to maintain a dark center (e.g., at least about −13 dB contrast) under focus. This effect originates from the same physics that causes 'vortex collapse' in traditional STED implementations when the OAM beam is not correctly circularly polarized. The dark center is of high importance to the resolution achievable by a STED system. The present inventors verified that it is possible to achieve −13 dB of intensity suppression compared to that of peak intensity of the donut, which is desirable for a viable STED beam. This was tested by imaging the focused donut using the reflection from 80 nm gold particles immobilized on a coverslip as described in Willig et al., Nat. Meth., 3, 721-23 (2006). A pellicle beamsplitter was used to split the reflection from the beam line and a photomultiplier tube (PMT) was used for detection. The results are shown in the image of section (a) of FIG. 3 and the graph of section (b) of FIG. 3. It was verified that it is possible to achieve −17 dB of intensity suppression compared to that of peak intensity of the donut, which exceeds the −13 dB threshold desirable for a viable STED beam (See also section (a) of FIG. 7).

Figure 4:
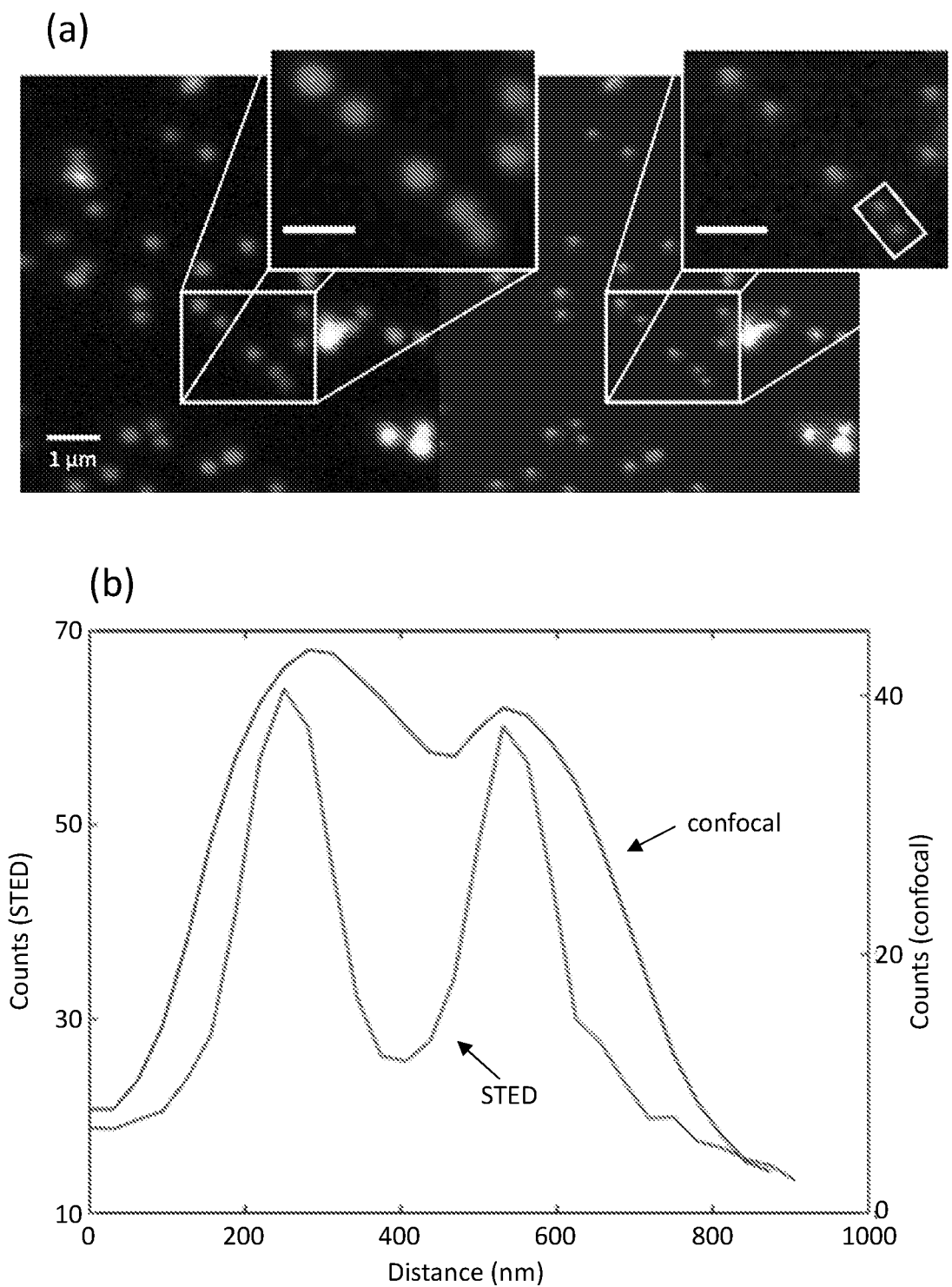
FIG. 4 provides in section (a) a comparison of confocal fluorescence microscopy (left) to STED microscopy (right) with an enlarged region of interest inset (inset scale bar is 700 nm), demonstrating a clear reduction in spot size with a calculated confocal resolution of 220+/−18 nm and a calculated STED resolution of 101+/−8 nm; and in section (b) a linecut of two beads (outlined in yellow) is shown on the right.

To measure the resolution of the fiber-coupled STED microscope of FIG. 1, fluorescent beads, 100 nm in diameter, were imaged and the resulting spot sizes fitted to a Gaussian. The average full width half max (FWHM) of the spot sizes was recorded and the resolution was calculated by taking into account the finite size of the beads. Sub-diffraction limited resolutions of 101+/−8 nm were achieved with an average STED laser power of 30 mW and an average excitation power of 1 μW, as measured prior to the objective. This was calculated using the 13 spots that were well-fitted by a Gaussian and not obviously composed of multiple beads. A comparison of confocal fluorescence microscopy and STED results is shown in FIG. 4. In summary, we have demonstrated sub-diffraction limited imaging using STED and excitation light carried through a single polarization-maintaining fiber. Resolutions of 101 nm have been achieved.

Figure 7:
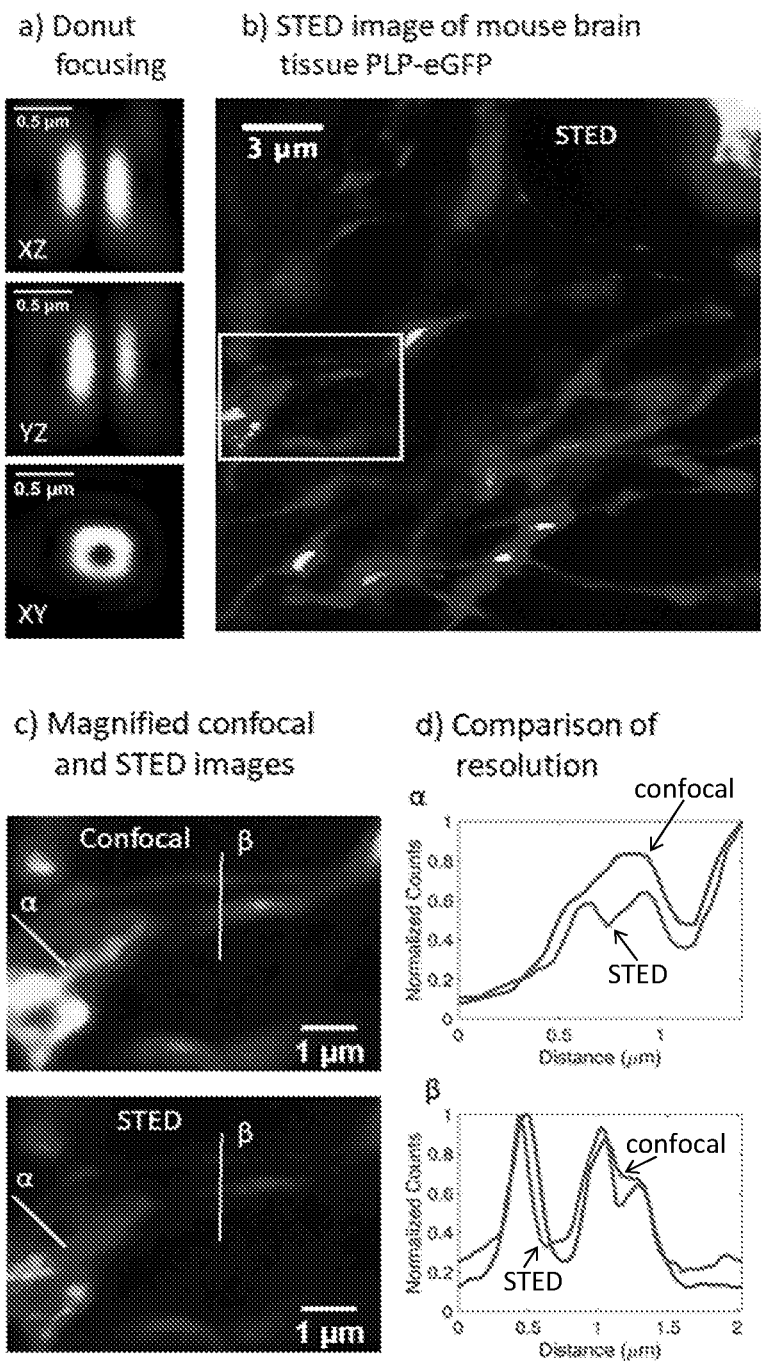
FIG. 7 provides data demonstrating fiber-coupled STED.

To test sensitivity in a biological sample, imaging of fixed mouse cortex with oligodendrocytes labeled with EGFP was performed. The fiber-coupled STED shows enhanced resolution compared with confocal and additional sub-diffraction limited structures can be clearly resolved. FIG. 7 provides data demonstrating fiber-coupled STED. Section a) shows the focusing of a donut beam generated from fiber, using an oil immersion NA=1.4, 100× objective onto a cover slide of immobilized gold nanoparticles of 80 nm diameter. Scattering from these nanoparticles was collected with the objective and detected with a photomultiplier tube (PMT) to image the point spread function (PSF) of the STED beam axially (XZ and YZ) and laterally (XY). Section b) provides an image of fixed cortex slice (PLP-eGFP mouse) using fiber-coupled STED and section c) provides a magnified comparison of confocal imaging vs. fiber-STED. Two lineouts of interest are labeled and plotted in section d) showing that features of the tissue that are unresolved using confocal microscopy become resolvable while using fiber-STED.

These findings enable the provision of a fiber-coupled stimulated emission depletion (STED) microscope with a compact footprint that can provide sub-diffraction limited resolution for in-vivo biological imaging or nanoscale patterning. Super-resolution microscopy and lithography are vital, both in terms of understanding biological systems, as well as in pursuit of smaller and higher performance electronic and photonic components to continue the advances predicted by Moore's law. In one aspect, the disclosure provides a compact and flexible fiber STED system, with resolution <80 nm, 3-4× below the classical diffraction limit in the visible, which provides the ability to push the current boundaries with great potential rewards. The fiber-coupled STED microscope systems of various aspects of the disclosure herein can be useful in a broad range from fundamental super-resolution studies of molecular interactions, cellular structure and function, synaptic formation in learning, to materials science applications.

Figure 5:
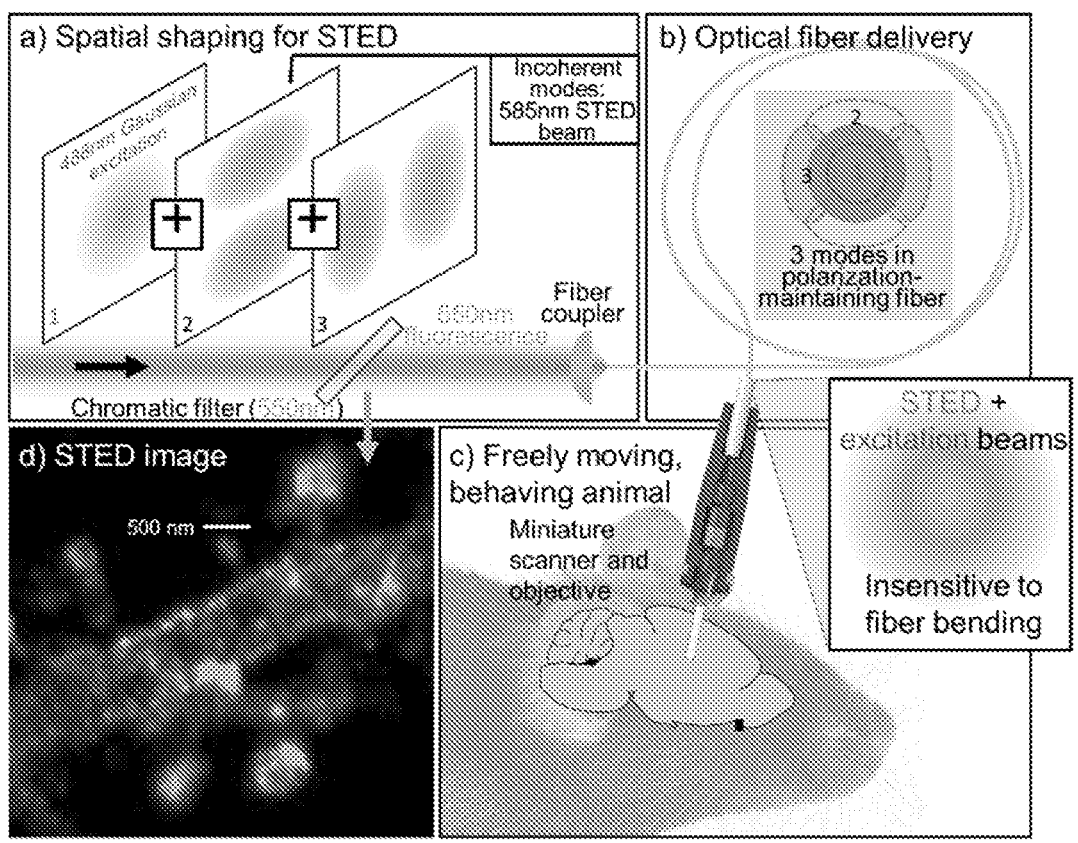
FIG. 5 provides a set of sections demonstrating a STED microscopy method of the disclosure. Section (a) shows a basic concept with a diagram of fiber-coupled STED microscope for high-resolution imaging of deep-brain structures in an awake behaving mouse. Lasers at 488 and 585 nm are shaped into a Gaussian and two orthogonal higher order Hermite Gaussian modes, respectively. In section (b), both lasers are launched into a flexible polarization-maintaining optical fiber, and are not affected by fiber bending. In section (c), the two wavelengths (one Gaussian and one donut beam with a clear central null) are focused through a microendoscope implanted in the brain of a freely moving animal. The microendoscope can include a miniaturized, high numerical aperture GRIN objective lens, relay optics, and compact technology for lateral scanning to construct an image at resolutions approaching ~80 nm. Section (d) provides an image taken on a benchtop STED microscope of hippocampal neuron dendrites.

FIG. 5 provides a set of drawings showing an example implementation. Section (a) shows the coupling of excitation (e.g., 488 nm) and depletion (e.g., 585 nm) beams into a polarization-maintaining optical fiber. The excitation beam is Gaussian, but the depletion beam is a donut beam, produced by adding up two modes incoherently in optical fiber, such that the output mode from the fiber is insensitive to bending. Section (b) shows the coiled fiber and a cross-sectional diagram of the overlapping modes of the excitation and depletion beams. See R. D. Niederriter, M. E. Siemens, and J. T. Gopinath, "Simultaneous control of orbital angular momentum and beam profile in two-mode polarization-maintaining fiber," Opt. Lett., 41(24), 5736-5739 (2016), which is hereby incorporated herein by reference in its entirety, discloses an example of a way to provide the donut-shaped depletion beam. As shown in section (c) of FIG. 5, a compact optical scanner and miniature objective focus the light onto the sample. The resulting fluorescence is collected back through the objective and coupled through the fiber. Section (d) of FIG. 5 shows an image taken on a benchtop non-fiber STED microscope of hippocampal neuron dendrites. The flexible fiber-coupled STED with a miniature objective described herein will allow super-resolved in vivo imaging in awake behaving animals as well as spectroscopy and lithography in situ (ex. cryostat).

Thus, in certain aspects, the present disclosure provides new capability in super-resolution microscopy: a fiber-coupled stimulated emission depletion (STED) microscope with a compact footprint that can provide sub-diffraction limited resolution for in vivo biological imaging, nanoscale patterning, and innovative spectroscopy. The compact and flexible STED systems described here, with resolution 3-4× below the classical diffraction limit in the visible, provide the ability to push the current boundaries with great potential rewards. Existing super-resolution imaging systems require bulky, fixed microscopes that are a non-starter for live animal imaging or endoscopy and cannot provide both the spatial and temporal resolution of STED. In contrast to other imaging technologies and instruments, the fiber-coupled STED microscope described herein will allow sub-100 nm resolution imaging in a compact, flexible format that is a leap above the capabilities of other super-resolution techniques. The technology has potential application for in vivo animal studies, endoscopy, as well as optical patterning and nanoscale spectroscopy.

One of the most powerful applications of the STED microscope is live cell imaging. STED microscopy has an advantage over other super-resolution techniques to break the diffraction barrier (e.g., Structured Illumination Microscopy (SIM), Photo-Activated Localization Microscopy (PALM) and STochastic Optical Reconstruction Microscopy (STORM)), in that it does not require computation from multiple images to attain sub-diffraction resolution. STED microscopy has now been routinely used for live cell imaging with genetically encoded fluorophores at frame rates as high as 30 frames/sec. In this application, it greatly outperforms PALM and fPALM, which are limited by the camera acquisition time with intrinsically slower image acquisition rates (0.04 frames/s). While live-cell SIM has achieved ~10 Hz imaging speed in a wide field, the spatial resolution in the lateral dimensions is 3× larger than the resolution that STED microscopy can achieve, which is insufficient for many of the applications described here. Some of the drawbacks of live cell STORM imaging are the inability to use genetically encoded fluorescent proteins and the need for special buffer solutions that can be toxic to cells. STED microscopy is the only super resolution technique shown to be effective for in vivo imaging in scattering tissue.

Moving from free-space (fixed to a bulky microscope head) to fiber optic-coupled STED system provides exciting new flexibility for this technique, opening the possibility for endoscopic and in vivo sub-diffraction limited imaging. The primary obstacle to fiber-based STED is that standard, commercially available step index fiber does not support the required OAM modes as eigenmodes. Progress has recently been made on a fiber-based STED microscope system using specialty vortex fibers, resulting in fluorescent spot sizes of 103 nm from calibrated samples. However, this requires custom vortex fibers that are expensive, difficult to obtain, and require significant design efforts.

Figure 6:
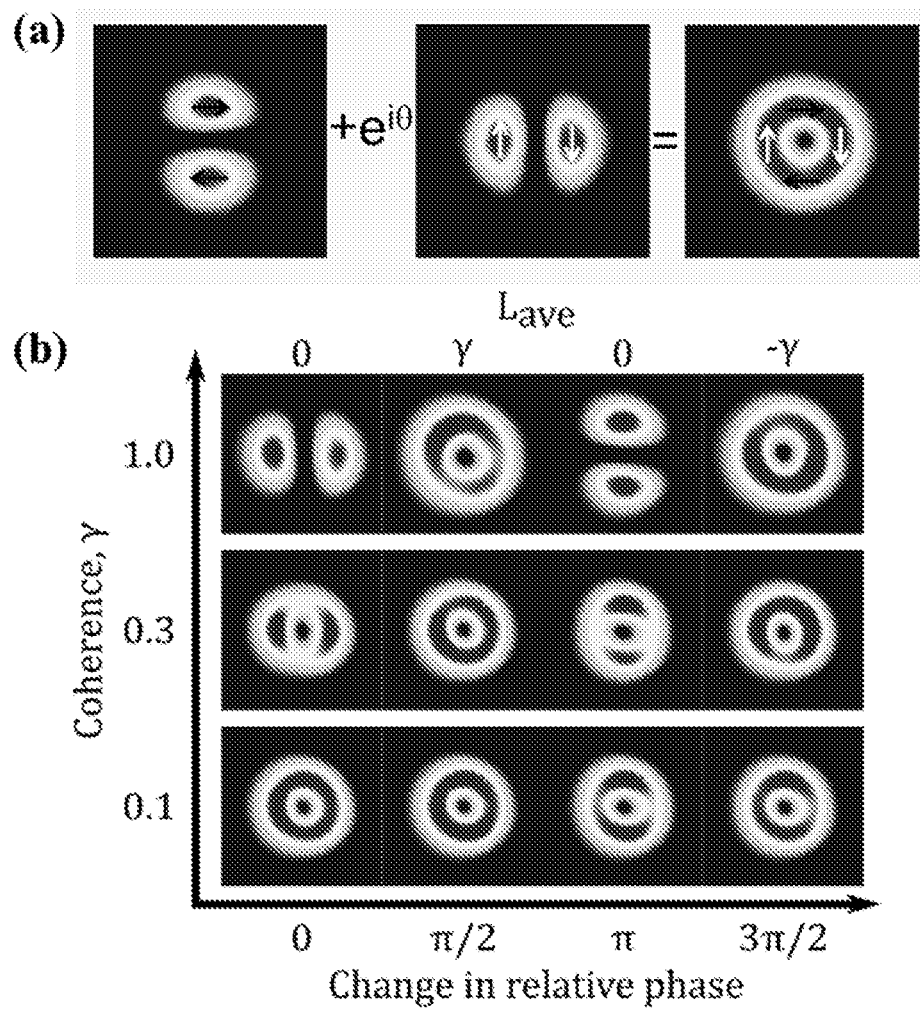
FIG. 6 provides a set of sections demonstrating the formation of a "donut" depletion beam. In section (a), two modes supported in polarization maintaining fiber are added to produce a beam with orbital angular momentum (OAM=+1 $\hbar$) if the phase between the modes (c) is 90°. Section (b) shows measured beam profiles corresponding to the degree of temporal coherence, $\gamma$, and relative phase between PM fiber modes, modulo 2π. For $\gamma \approx 1$, the intensity pattern changes between donut and two-lobed shapes depending on the relative phase. As the temporal coherence between modes decreases, the beam profile depends less on the relative phase. For $\gamma \ll 1$, the beam profile is insensitive to the relative phase. Throughout, dark portions at the centers of toroids represent intensity minima, but the dark portions in the middle of the arcuate portions of the toroids and at the centers of paired lobes are intensity maxima.

In an attractive alternative scheme for transmitting donut-shaped radiation in an optical fiber, beams with OAM have been produced with polarization maintaining fiber by coupling to orthogonal Hermite-Gaussian (HG)-like linear-polarized modes, as shown in section (a) of FIG. 6. For example, present inventors and their coworkers have demonstrated that by adding two linearly polarized modes in polarization maintaining fiber, tunable OAM can be generated over the range of ±2 and ±1 h by controlling the phase between the summed modes. This technology is described in R. D. Niederriter et al., "Continuously tunable orbital angular momentum generation using a polarization-maintaining fiber," Opt Lett, 41(14), 3213-16 (2016); B. M. Heffernan et al., "Tunable higher-order orbital angular momentum using polarization-maintaining fiber," Opt Lett, 42(14), 2683-86, (2017); R. D. Niederriter et al., "Generation of tunable orbital angular momentum in polarization maintaining fiber," Presented at Frontiers in Optics (FiO), FTh5B.2 (2016); and B. M. Heffernan, et al., "Generation of higher-order orbital angular momentum in polarization-maintaining fiber," Presented at Conference on Lasers and Electro-Optics (CLEO), STu4K.3 (2017), each of which is hereby incorporated herein by reference in its entirety. While this clear phase control can be useful in some applications, dependence of the output donut for STED microscopy on the relative phase of the modes makes the system very sensitive to perturbation. Thus, this method alone is not highly advantageous for fiber STED because real-time adjustments would be needed to account for phase changes introduced by fiber movement.

However, the present inventors have determined that when the two fiber modes that compose the donut are have low temporal coherence, a donut beam with substantially no dependence on relative phase is generated. This is demonstrated in section (b) of FIG. 6, in which the lower the coherence, the more insensitive the beam profile is to phase difference. This "incoherent donut" is insensitive to fiber conditions, and can provide a robust, high-quality, and stable STED beam, even under dynamic fiber bending. This method can advantageously be used in the fiber-based STED microscopes described herein. The present inventors have determined that if these two modes are temporally incoherent, a donut-shaped beam with no dependence on relative phase can be realized and hence is substantially insensitive to fiber conditions. The present inventors have determined that this technique would be especially useful in the provision of fiber-based STED microscopy methods and systems.

The STED microscope systems of the disclosure can be modeled after demonstrated STED microscope systems, but with some important differences: (1) Inclusion of optical fiber to deliver both the excitation and depletion beams with the proper spatial profile and low coherence and (2) Fluorescence collection back through the same optical fiber. FIGS. 1 and 5 provide diagrams of overall experimental setups. A pulsed laser beam at 488 nm can be used for excitation of GFP/YFP. The depletion light can be generated by a synchronized pulsed 585 nm laser. Both beams are coupled into a polarization maintaining fiber, which will preserve their linear polarization in fundamental and higher order modes without significant dependence on fiber bending.

In certain embodiments of the systems as described herein, a miniature microscope objective can replace a conventional objective, improving functionality for in vivo imaging or endoscopy. In certain such embodiments, the fiber can be connected to a miniature microendoscope that includes miniature lenses, scanning device, and an objective lens. The microendoscope can be designed to weigh <4 grams to enable use for attached brain imaging in behaving animals. The excitation beam will focus to a diffraction-limited spot while the STED beam will focus to a "donut" mode with a null in the center through a specially-designed achromatic lens assembly with a numerical aperture (NA) of 0.8 and a field of view of ~70 microns.

In certain embodiments, the excitation light can be a short-pulsed infrared laser for two-photon excitation fluorescence in combination with the STED depletion beam. For GFP or YFP, the two-photon excitation wavelength is typically 900-950 nm (GFP) and 900-1050 nm (YFP) using short pulses ~200 femtoseconds in duration operating at 20-80 MHz. Two-color STED imaging has been demonstrated using two-photon excitation with a short pulsed laser at 910 nm, 200 fs and a depletion (STED) laser at 592 nm, ~100 ps pulse duration for simultaneous imaging of GFP and YFP labeled neurons. The fiber-STED microscope described herein utilizes a polarization maintaining fiber with a core size that permits IR wavelength single mode propagation, making this technique compatible with two-photon STED microscopy after compensation of the fiber dispersion. STED microscopy using two-photon excitation has key benefits over one photon visible excitation due to the reduced scattering of light at the longer wavelengths. Additionally two-photon STED has been demonstrated for live imaging with improvements over one-photon STED. Two-photon STED is further described, for example, in Drobizhev, M. et al. "Two-Photon Absorption Properties of Fluorescent Proteins." Nature Methods 8(5), 393-99 (2011); Bethge, P. et al., "Two-photon excitation STED microscopy in two colors in acute brain slices," Biophys J. 104(4), 778-85 (2014). doi:10.1016/j.bpj.2012.12.054; and Takasaki, K. T. et al., "Live-cell superresolution imaging by pulsed STED two-photon excitation microscopy," Biophys J., 104(4), 770-77 (2014); Moneron, G. et al., "Two-photon excitation STED microscopy," Opt. Express. 17(17), 14567-73 (2009).

Figure 8:
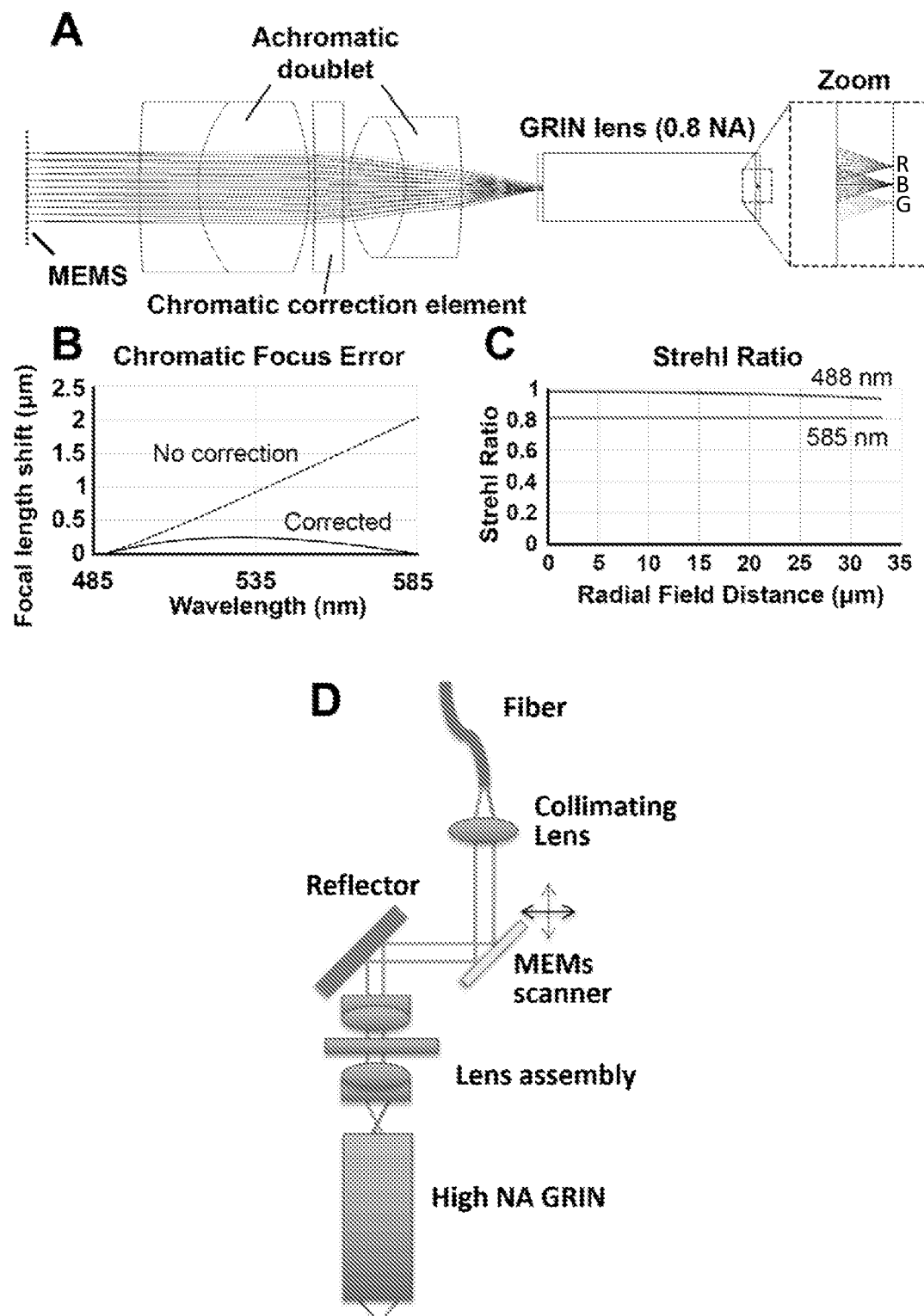
FIG. 8 shows an example of a design of a STED microendoscope.

An example of a design of a STED microendoscope is shown in FIG. 8. An achromatic lens is used to collimate excitation and STED light out of the fiber, and next, a scan lens and relay lens will send the light from the MEMS scanner to the objective lens. Microendoscope design. (A) Zemax optical system design for chromatic correction of axial focus. (B) With chromatic correction, the focal shift is under 0.5 microns. (C) Off-axis performance of the system showing >0.8 Strehl ratio for chromatic correction of axial focus including doublets, refractive element, and GRIN lens assembly.

An initial Zemax design for the imaging system (including doublets, refractive element, and GRIN lens assembly (high NA GRIN objective lens (Part #GT-MO-080-0415-488, GRINTech Inc.)) is shown to provide tight focusing in a compact design in sections (a), (b) and (c) of FIG. 8. Section (b) demonstrates that the focal shift is under 0.5 microns. Section (c) shows a Strehl Ratio at least 0.8 over a broad field distance. A. Section (d) of FIG. 8 shows a schematic of microendoscope. The system can be built from two connecting sections so that the implanted GRIN lens can be detached from the miniature scanner and lens assembly when imaging is not required. Further details of exemplary systems can be as provided in W. Zong et al., "Fast high-resolution miniature two-photon microscopy for brain imaging in freely behaving mice," Nature Methods, 14(7), 713-19 (2017), which is hereby incorporated herein by reference in its entirety. While various embodiments use a MEMS scanner, other scanners, such as piezoelectric scanners can be used.

It is highly desirable that the excitation and depletion laser focal spots are aligned within the expected resolution of the system, both axially and laterally. Typical GRIN lens assemblies are designed to operate at single wavelengths, and can cause significant misalignment at the different wavelengths of 488 and 585 nm. Optical modeling, using Zemax optical design software, shows that the chromatic focusing errors from the GRIN lenses can be eliminated by custom lens assemblies. Two stock achromatic doublet lenses (Edmund Optics #49-271 and #65-568) and a custom glass concave lens (chromatic correction element) can be used to balance the chromatic aberrations of the GRIN lens (section (a) of FIG. 8). In the model, excellent alignment was achieved at the two wavelengths with <0.5 µm focal shift between the two colors. The STED super-resolution regime also desires minimal geometric aberrations over the full field of view (FOV) which can be undesirable when imaging off axis with a GRIN lens. The system of this embodiment is designed to use only the highest-performance region of the full GRIN lens FOV, which is normally ~120 µm. The initial design shows minimal off-axis distortions over a field of view (FOV) of 70 µm. The Strehl ratio for the excitation beam is ~1 over a range of 70 microns. The Strehl ratio of the 585 nm light is ~0.8 in this field-of-view, which is close to diffraction-limited and can be further improved if needed with the use of more custom lenses. This design thus shows that chromatic correction and high NA focusing can be met by using carefully designed optical elements.

Of course, other designs can be used. For example, larger aperture optics can be used for imaging through a cranial window, to minimize distortion.

The resolution enhancement from STED microscopy can be calculated from the known theory of the STED process and is given by the following equation:

$$\Delta x = \frac{\lambda}{2NA\sqrt{1+\frac{I_{STED}}{I_{SAT}}}}$$

where $\lambda$ is the wavelength (585 nm), NA is the numerical aperture, $I_{STED}$ is the maximum intensity of the STED donut beam and $I_{SAT}$ is the intensity at which half of the excited molecules are depleted by stimulated emission process. $I_{SAT}$ for common fluorophores typically ranges from 10-20 MW/cm$^2$. The STED depletion beam in one embodiment of the systems of the disclosure has an average power at the sample of 10-20 mW, with a repetition rate of 20 MHz, giving a pulse energy of 0.5-1 nJ. For this pulse energy, the maximum STED intensity, $I_{STED}$ is calculated to be around 0.1 GW/cm$^2$, given the pulse duration (~1 ns) and the STED mode size (approximately 4× larger area than the diffraction limited spot size of 300 nm for a miniature objective NA of 0.8). Thus, it is possible to achieve a 3 to 4-fold improvement over standard confocal imaging, with ~80 nm resolution for the disclosed miniature microendoscope design.

Fluorescence emission can be collected and transmitted for detection through the optical fiber. The fiber core itself can provide the confocal pinhole desired for axial sectioning. The emission can be separated from the excitation and STED using a dichroic mirror and detected with a sensitive avalanche photodetector. In embodiments using the optical assembly described above, fluorescence can be transmitted through the high NA GRIN objective lens then relayed back through the same optics as the excitation, descanned by the MEMs scanner and focused back into the same fiber, greatly simplifying the system. Of course, in other systems of the disclosure, the fluorescence emission is collected differently, e.g., through a separate optical fiber.

The compact microendoscope can also be designed for a variety of applications including flexible nanoscale lithography by mounting on an adjustable xyz and rotation stage. Additional designs can be constructed depending on the users' experimental requirements. For example, imaging in deeper brain areas such as the nucleus accumbens and piriform cortex will require a longer length GRIN lens that can be included with modified optical designs.

A fiber-STED microscope described herein can be used, for example, to image hippocampal dendritic spines using ex vivo brain slices. The slices are generated from Thy1-YFP mice and the tissue is incubated in artificial cerebral spinal fluid (aCSF) solution during imaging. STED imaging of YFP can first be performed with a bench-top STED microscope and the same area of the sample can be imaged with the fiber-coupled STED microscope of the disclosure, in order to compare the depth of imaging achievable, signal to noise ratio, imaging area and resolution. For brain imaging in vivo, the GRIN lens is attached to the skull by dental cement after performing a small craniotomy. For imaging in layer 1 of the brain, the lens can be placed on the surface of the brain. For imaging in deep brain regions, the small diameter GRIN lens can be inserted into the brain, using a similar procedure as in R. P. Barretto and M. J. Schnitzer, "In vivo optical microendoscopy for imaging cells lying deep within live tissue," Cold Spring Harb Protoc, 2012(10), 1029-34, (2012), which is hereby incorporated herein by reference in its entirety.

In another experimental study, a STED microscope was used to acquire not only through-fiber STED images of fluorescent beads, but also biological samples. These images indicate a typical resolution of 116 nm. This result sets the stage for future awake-behaving brain imaging with sub-diffraction-limited resolution.

Figure 9:
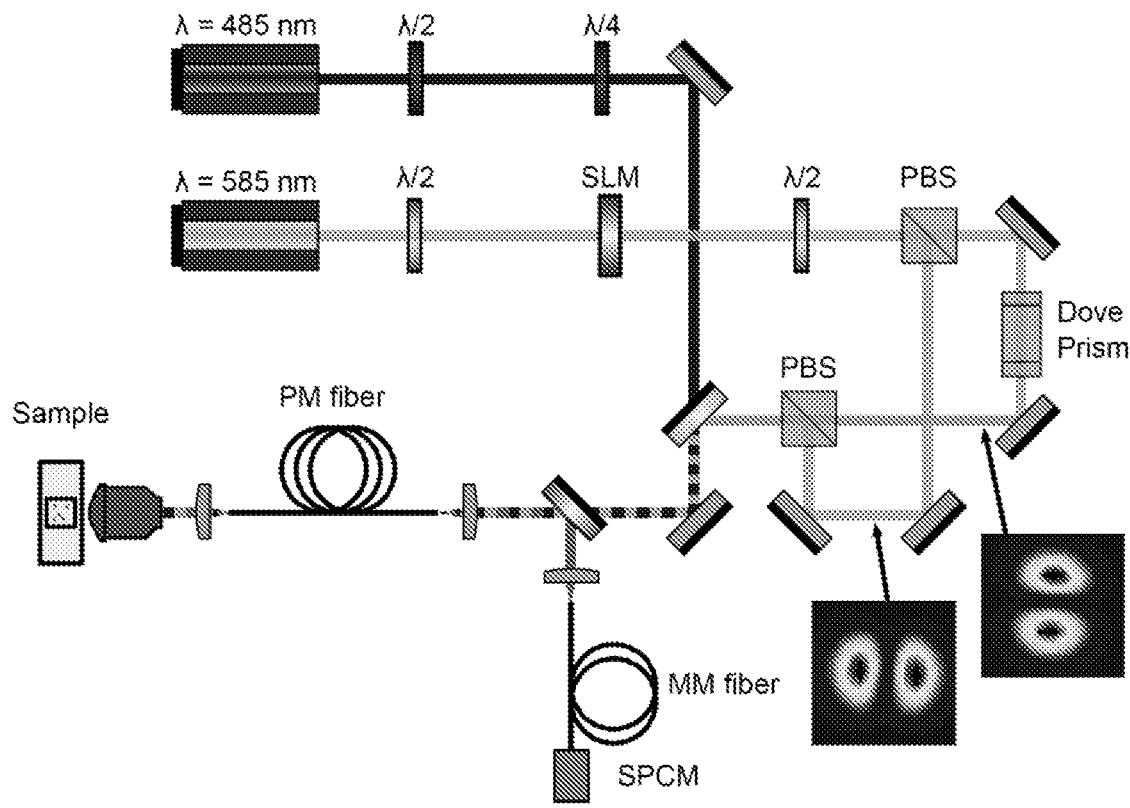
FIG. 9 provides a diagram of the fiber STED microscope. Fluorophores are excited at 485 nm and depleted at 585 nm. The lasers have a repetition rate of 20 MHz. The STED laser (at 585 nm) is shaped to match the P M01 mode using a spatial light modulator (SLM). A polarizing cube beamsplitter (PBS) splits the beam into a Mach-Zehnder interferometer. In one arm, a dove prism rotates the spatial profile of the laser and introduces a delay of 74 ps. The transverse modes of the two STED beams are pictured, with the polarization indicated by black arrows. These beams are combined using another PBS and coupled to PM fiber (two meter length). The excitation light is sent through quarter and half-wave plates to control its polarization and then a high-pass dichroic mirror combines it with the STED light. Upon exiting the fiber, the STED and excitation beams are collimated and focused onto a fluorescent sample using a 1.4 NA, oil-immersion objective. This objective collects and collimates fluorescence, which is then coupled back into the PM fiber. A dichroic mirror splits the fluorescence from the common beam path. The light is passed through two chromatic filters and then focused into a multimode (MM) fiber coupled to a single photon counting module (SPCM).

The STED microscope used in these experiments, shown in schematic view in FIG. 9, was constructed almost entirely from off-the-shelf parts and is analogous in design to typical confocal fluorescence microscopes. Fluorescence is excited using 500 ps pulses of excitation radiation having a wavelength of 485 nm (from a PicoQuant LDH-P-C-485B). These pulses of excitation radiation are temporally overlapped with 1 ns pulses of depletion radiation having a wavelength of 585 nm (from a Mobius Photonics Rainbow-7-20 MHz). Both lasers have a repetition rate of 20 MHz. To efficiently couple light into the fiber, the depletion laser is shaped to match the PM$_{01}$ LG mode using a spatial light modulator (Meadowlark Optics, Standard 1920×1152 Nematic SLM System). The depletion radiation then passes through a half-wave plate, and a polarizing cube beam splitter (PBS) separates it into two arms of a Mach-Zehnder interferometer. In one arm, a Dove prism rotates the spatial profile by 90 degrees and delays the pulse by approximately 74 ps. The coherence time for the STED laser is estimated from the laser linewidth to be 2 ps. A second PBS recombines the two depletion radiation beams. A quarter-wave plate followed by a half-wave plate controls the polarization of the excitation beam, and a high-pass dichroic mirror (Chroma ZT561sprdc) combines it with the depletion radiation beam path. All three beams are coupled into a loosely coiled optical fiber (Thorlabs P1-980PM-FC-2) with a bend radius of approximately 50 mm. The fiber supports 6 modes at 585 nm; three different transverse profiles with two possible polarizations for each transverse mode. Twelve modes are supported at 485 nm. Care is taken to couple the excitation light into a Gaussian-like mode, which propagates without intermodal coupling over the 2 m fiber length. An apochromatic objective (Mitutoyo 10× plan apochromat) collimates the output of the fiber, which is then directed into an oil immersion, 100×, 1.4 NA microscope objective (Olympus UPLSAPO 100XO). A piezo stage (Mad City Labs Nano-LP100 XYZ) raster scans the sample in three dimensions through the focus.

The high-NA objective collects and collimates fluorescence from the sample, which then retraces the path of the STED and excitation beams before being coupled into the polarization-maintaining optical fiber. The counterpropagating fluorescence is collimated after exiting the fiber and split from the beam path using a dichroic mirror (Chroma T525/50dcrb) that reflects fluorescent wavelengths. The light is then passed through two chromatic filters (Semrock SP01-561RU-25 and FF01-520/35-25) so as to detect only fluorescent light. A fiber-coupled single photon counting module (SPCM)(Excelitas SPCM-AQR-15) detects and counts fluorescent photons for a variable exposure/pixel dwell time, typically 50 microseconds.

Figure 10:
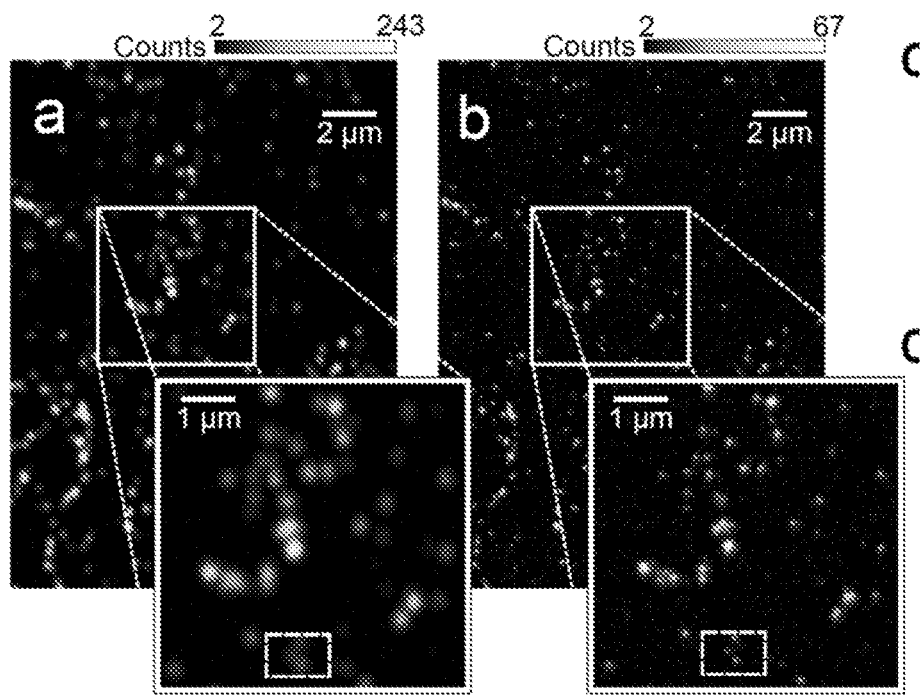
FIG. 10 provides Images of 45 nm fluorescent beads attained using (a) confocal and (b) STED modality. There was approximately 45 mW of power in the STED laser before the objective. The pixels size is 19.5 nm. These images have been convolved with a small Gaussian (waist of 0.8 pixels) for smoothing and the background has been subtracted to enhance clarity. A magnified area of interest is shown.
Figure 11:
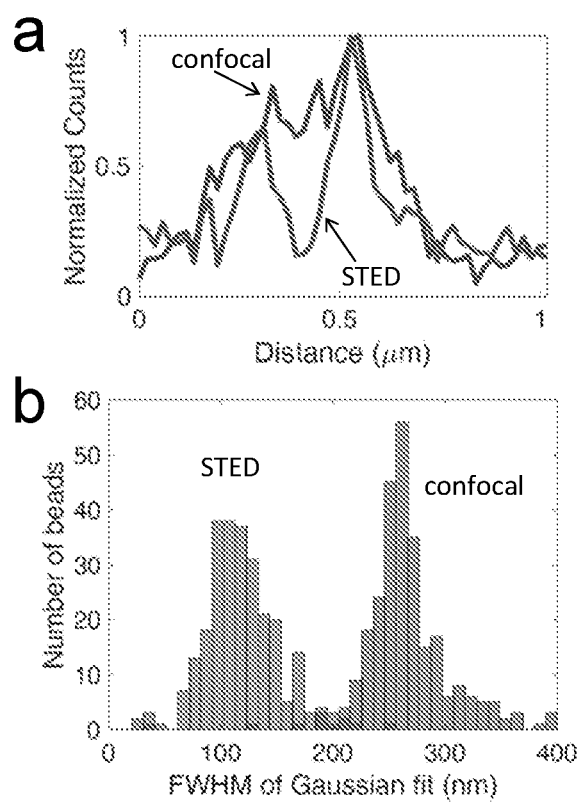
FIG. 11 provides (a) a cross sectional cut of the boxed region of FIG. 10 within the magnification; and (b) a histogram of Gaussian-fitted FWHM values for bead images. The confocal distribution has a median of 260 nm, while the STED distribution has a median of 116 nm. This demonstrates more than a two-fold improvement of resolution from confocal. The graphs of FIG. 11 were derived from raw data.

Proof-of-concept images demonstrating a more than two-fold improvement in resolution compared to confocal modality were attained from both fluorescent test targets and biological samples. Images of 45±6 nm fluorescent beads (Invitrogen FluoSpheres F8795) were taken using approximately 45 mW of STED light and 7 µW of excitation, as measured before the objective. Results are shown in FIG. 10, in which section (a) shows images using confocal microscopy and section (b) shows images using STED microscopy as described here. The pixels size is 19.5 nm. These images have been convolved with a small Gaussian (waist of 0.8 pixels) for smoothing and the background has been subtracted to enhance clarity. A magnified area of interest is identified. A clear improvement in resolution over confocal imaging can be seen, with closely spaced beads becoming distinguishable when using STED. Section (a) of FIG. 11 provides a graph of a cross sectional cut of the identified region of section (b) of FIG. 10. The resolution of a STED system depends on the properties of the fluorophore in use and on the conditions to which the molecules are subjected. This makes it difficult to assign a resolution to the STED system. However, as an estimate, Gaussians are fitted to the images of the fluorescent beads and used to define the resolution as the full width half max (FWHM) of the fitted Gaussian. This is done algorithmically using a peak-finding code to define a region of interest centered on a bead. Peaks that are too close together are omitted in order to get accurate fits. This yields distributions of FWHM values, shown in the histogram of section (b) of FIG. 11. The median of this distribution is taken as the typical resolution. This procedure gives an estimated resolution of 260±7 nm confocal and 116±6 nm STED. The finite size of the beads is not taken into account, so the resolution derived from the FWHM of imaged beads represents an upper limit estimate of the true resolution of the STED microscope. The uncertainty in median values of these distributions is due to variations in the input parameters of the peak finding code that can produce slightly different outcomes.

Figure 12:
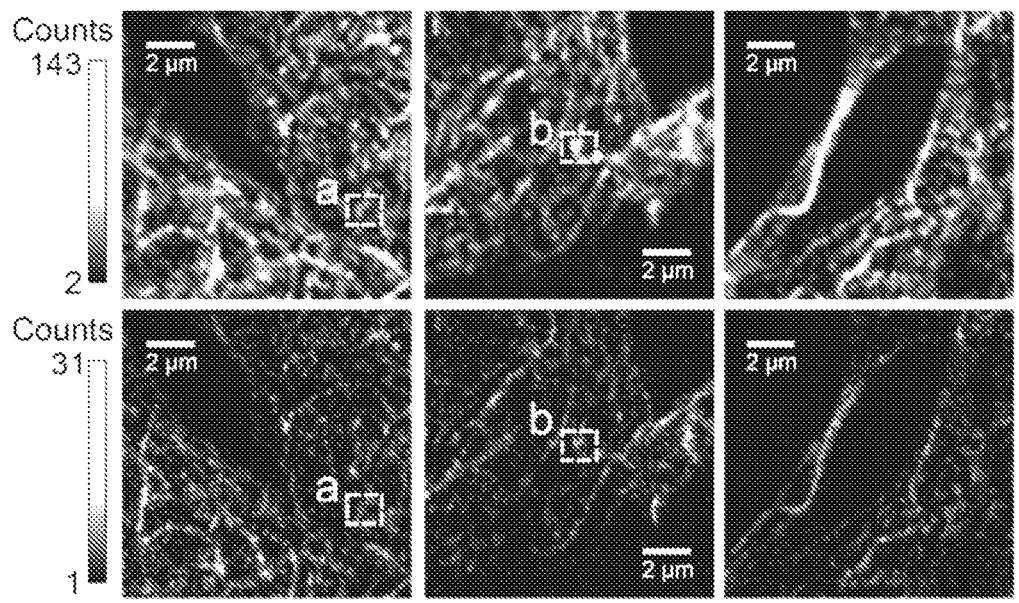
FIG. 12 provides images of HeLa cells immunostained for tubulin using Alexa 488. The images have been convolved with a Gaussian with a waist of 0.8 pixels (39 nm) for smoothing and the background was subtracted. The top row are confocal images and the bottom row are STED.
Figure 13:
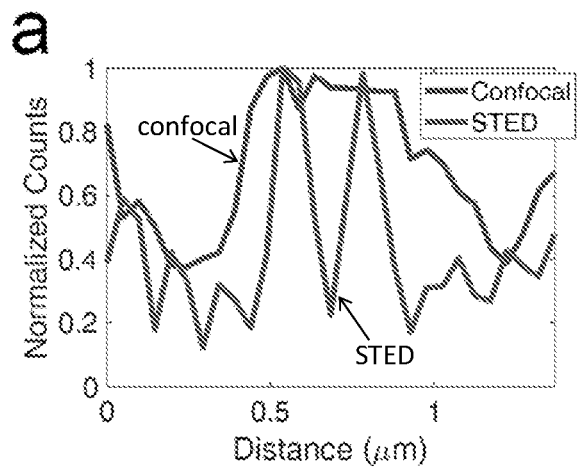
FIG. 13 provides normalized linecuts of raw data are shown in (a) and (b), demonstrating at least a two-fold improvement resolution. The pixel size is 48.8 nm and proximately 20 mW of STED and 6 μW of excitation power were used, measured before the objective.
Figure 13:
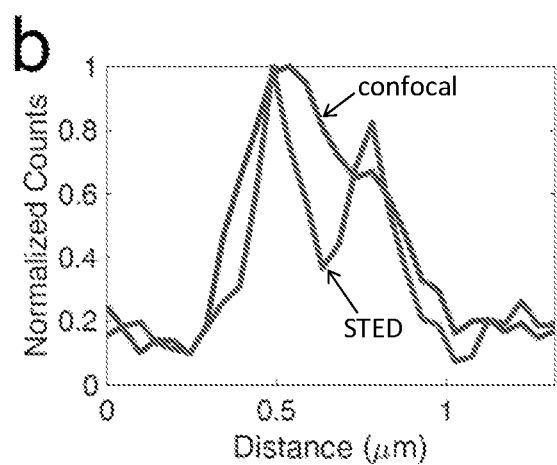

While images of fluorescent beads are well-suited for resolution estimation, the true test of a STED system is its ability to image biological samples. Thus, images of tubulin immunostained with Alexa 488 in fixed HeLa cells were imaged using the system. These images are shown in FIG. 12. The images have been convolved with a Gaussian with a waist of 0.8 pixels (39 nm) for smoothing and the background was subtracted. The top row are confocal images and the bottom row are STED. Compared to confocal, a clear improvement in resolution is seen, with features and their morphologies becoming more distinguishable in the STED case, including structures as small as 120 nm. Normalized linecuts of raw data are shown in sections (a) and (b) of FIG. 13 (confocal and STED, respectively), demonstrating at least a two-fold improvement resolution. The pixel size is 48.8 nm and proximately 20 mW of STED and 6 µW of excitation power were used, measured before the objective.

The experiments also demonstrated that this method of fiber STED microscopy yields condition-independent resolutions. This robustness is essential for practical deployment of fiber STED microscopy for in vivo applications, such as the study of brain function in freely moving animals. Theoretically, the STED beam should be insensitive to fiber conditions in the limit that the two fiber modes making up the STED doughnut are completely incoherent with respect to one another. As an initial test, the two STED beams were coupled into the fundamental mode of the PM fiber and the interferometric visibility was measured. A piezo delay stage was used to scan the relative phase between the two beams, resulting in a fringe visibility of 3%. This indicates very minor mutual coherence between the two STED modes and that the output of the fiber will not substantially change with bending or heating. Accordingly, the person of ordinary skill in the art will recognize that, as used herein, the term "temporally incoherent" does not require theoretically perfect temporal incoherence, but rather can allow for some minor degree of incoherence as described below.

Figure 14:
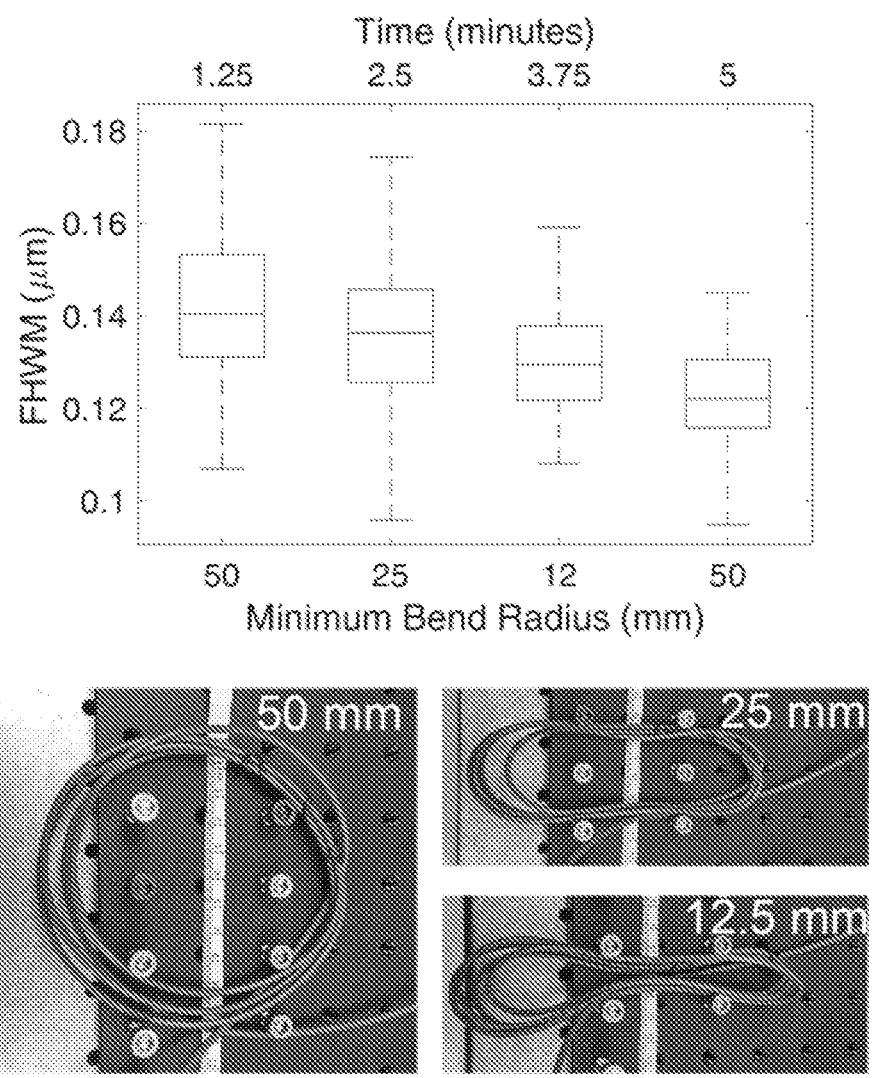
FIG. 14 provides a box plot of the measured FWHM of bead images for 100 nm fluorescent beads. The center line in each box gives the median of the data set. Note that while the distribution of FWHM's changes, this is caused by a time drift in the z-axis of the stage rather than by changes in fiber conditions. Below are images of the fiber in bent states, with minimum bend radius marked.

Next, in a more rigorous test 100 nm fluorescent beads (Invitrogen FluoSpheres F8803) were imaged four times in a row, as the fiber was bent into different configurations between frames. Each image took approximately 75 seconds to acquire, and the total time elapsed for the measurement was 5 minutes. The first frame was taken with the fiber in its typical resting position (50 mm bend radius), as was the last to control for photobleaching, drift of the piezo stage in the z direction, or any drift in alignment into the fiber that could occur during the time lapse between acquisitions. The resulting distribution of FWHM values was found to change over the course of the measurement due to one of these drift effects, but not bending, as shown in FIG. 14. This conclusion is inferred from the observation that the resting bend radius of the fiber does not produce the same results at the beginning and end of the measurement. The test demonstrates that the presently-described approach to fiber STED microscopy produces a robust platform, in agreement with theoretical considerations.

The strategy of using linear polarization for the STED doughnut has consequences for the operation of our microscope, as fluorophores can exhibit sensitivity to both excitation and STED polarization. Consider a fluorophore with a given orientation of its dipole moment. It is optimally excited when the polarization of the excitation light is parallel to the dipole moment, with decreasing probability of excitation as a relative angle forms between them. The excitation light therefore is advantageously circularly polarized in order to ensure that at some point during every cycle of light, the polarization and dipole moment are parallel. This argument can similarly be applied to the STED light causing de-excitation via stimulated emission. However, the fiber (STED) modes are desirably remain linearly polarized to maintain a dark center, and so cannot deplete fluorophores as efficiently as circularly polarized STED beams across its full spatial extent. This can result in asymmetric images for single molecules, because fluorescence is not depleted in places where the STED beam is polarized perpendicular to the dipole moment of the molecule. This phenomenon has been leveraged in other STED microscopes to gain information about the orientation of molecules in a target, resulting in molecular orientation microscopy using STED (MOM-STED). This capability is fundamental to our microscope. However, we expect that the STED polarization constraint should not play a large role in situations where fluorophores are able to freely rotate, where there are many randomly oriented fluorophores, or for an objective with a smaller numerical aperture. In low NA situations, the polarization of the doughnut mode is far less crucial because the focus is not tight enough to collapse nodal features, and so in principle the STED polarization could be made circular.

Based on the description herein, the STED microscopy systems and methods of the disclosure can provide a number of. Foremost among these is improving the signal-to-noise ratio. There is an inherent loss of signal in any fiber-coupled microscope due to fiber coupling of the fluorescence. Recently, double-clad fibers have been deployed in conventional fluorescence microscopes that allow for more efficient signal collection. Equally important is reducing noise sources associated with fiber. Large backgrounds have been observed, possibly caused by laser pulses reflected from the fiber facet and collimated using the coupling lens. Another possible background source is autofluorescence within the fiber. In the future, these noise sources might be mitigated through time correlation photon counting techniques or refined detection schemes. Resolution can be improved by increasing power in the STED beam, which is currently limited to about 45 mW time averaged. We have Our fiber STED microscope can readily be made into an all-fiber implementation where the higher-order fiber modes are excited from the fundamental using long-period Bragg gratings to provide more robust and alignment-tolerant operation. Our microscope also provides a basis for the creation of a fiber two-photon STED system that would provide deep tissue super-resolution in awake and freely-behaving animals.

In certain embodiments of the methods and systems as otherwise described herein, the central mode of the polarization-maintaining optical fiber has a maximum at the center thereof, e.g., as in a substantially Gaussian mode. In certain embodiments, the central mode is a fundamental mode.

In certain embodiments of the methods and systems as otherwise described herein, the depletion radiation is propagated in two orthogonal modes of the polarization-maintaining optical fiber. These orthogonal modes can be, for example, Hermite-Gaussian modes (e.g., having at least one odd numbered identifier, such as 0.1; 1.0; 2.1; 1.2). But other modes, especially modes having two lobes disposed about a central null, can be used.

In certain embodiments of the methods and systems as otherwise described herein, the depletion radiation is propagated in the polarization-maintaining optical fiber with substantial orbital angular momentum. However, in certain alternative embodiments as otherwise described herein, the depletion radiation is propagated in the polarization-maintaining optical fiber without substantial orbital angular momentum In certain embodiments of the methods and systems as otherwise described herein, the depletion radiation is in the shape of a toroid. Such a toroid can be formed, for example, from the summation of two orthogonal HG or similarly-shaped modes.

As described above, in various aspects of the methods and systems of the disclosure, the depletion radiation propagates substantially temporally incoherently in one or more (e.g., at least two, or two) peripheral modes of the polarization-maintaining optical fiber. As noted above, this does not require perfect theoretical incoherence. Rather, some degree of temporal coherence is acceptable, as long as it results in a desired degree of bend insensitivity. For example, in certain embodiments of the methods and systems as otherwise described herein in which depletion radiation is propagated in two or more modes, the temporal incoherence ($\gamma$) between the modes is no more than 0.3, e.g., no more than 0.2, no more than 0.15, or no more than 0.1.

The depletion radiation desirably has a high degree of intensity contrast, so that it can strongly inhibit fluorescence at the periphery of the excitation radiation but not substantially inhibit fluorescence at the center of the excitation radiation. Accordingly, in certain embodiments of the methods and systems as otherwise described herein, the depletion radiation (i.e., as propagating in the fiber and/or as delivered at the object) has a contrast (i.e., from maximum intensity to minimum intensity at the center) of at least 13 dB, e.g., at least 15 dB, or at least 17 dB. In certain embodiments of the methods and systems as otherwise described herein, the depletion radiation has a central dark portion having a −5 dB width at the object (i.e., as compared to the intensity maximum) that is in the range of 25 nm-300 nm in width, e.g., 25-200 nm, or 25-100 nm, or 50-300 nm, or 50-200 nm, 50-100 nm, or 75-300 nm, or 75-200 nm, or 100-300 nm, or 100-200 nm in width. n certain embodiments of the methods and systems as otherwise described herein, the depletion radiation has a central dark portion having a −10 dB width at the object that is in the range of 10-150 nm in width, e.g., 10-125 nm, or 10-100 nm, or 10-75 nm, or 20-150 nm, or 20-125 nm, or 20-100 nm, or 20-75 nm, or 40-150 nm, or 40-125 nm, or 40-100 nm, or 40-75 nm in width.

As described above, the intensity maximum of the excitation radiation at the object desirably falls within a central dark portion of the depletion radiation at the object.

The person of ordinary skill in the art will, based on the description herein, overlap the depletion radiation with the periphery of the excitation radiation such that it provides a desired narrow effective excitation spot at the object. For example, in certain of the methods and systems as otherwise described herein, the depletion radiation and the excitation radiation overlap to provide an effective excitation spot at the object (i.e., having the ability to cause fluorescence of the object) that is substantially smaller than the diffraction limit for the optical system (e.g., a full-width at half-maximum of no more than 75%, e.g., no more than 50%, or no more than 30% of that of the diffraction limit). In certain such embodiments of the methods and systems as otherwise described herein, the effective excitation spot has a diameter of no more than 200 nm, e.g., no more than 150 nm or no more than 125 nm, or in the range of 10-200 nm, e.g., 10-150 nm, or 10-125 nm., or 50-200 nm, or 50-150 nm, or 50-125 nm, or 100-200 nm, or 100-200 nm.

The excitation radiation can be provided to the polarization-maintaining optical fiber in a number of ways; the embodiments described above are merely examples. In certain embodiments of the methods and systems as otherwise described herein, propagating excitation radiation of the fluorescence excitation wavelength in a central mode of the fiber comprises providing excitation radiation from a source of excitation radiation (e.g., a laser, or a filtered broadband source, or an amplified spontaneous emission source, or a laser diode) and coupling the excitation radiation into the central mode of the fiber (e.g., by focusing the excitation radiation onto a central portion of an endface of the optical fiber).

Similarly, depletion radiation can be provided to the polarization-maintaining optical fiber in a number of ways; the embodiments described above are merely examples. In certain embodiments of the methods and systems as otherwise described herein, propagating depletion radiation of the fluorescence depletion wavelength comprises providing depletion radiation from a source of depletion radiation (e.g., a laser, or a filtered broadband source, or an amplified spontaneous emission source, or a laser diode) and coupling the depletion radiation into the one or more peripheral modes of the fiber (e.g., by focusing the depletion radiation onto a peripheral portion of an endface of the optical fiber).

A variety of methods can be used to provide a desired toroidal shape (or other shape with an central intensity minimum. In certain embodiments as otherwise described herein, coupling the depletion radiation into the one or more peripheral modes of the fiber includes shaping the radiation into a profile having an intensity minimum in a central portion thereof, (e.g., in an appropriate Hermite-Gaussian mode such as 1.0 or 0.1), for example, using a spatial light modulator; separating the shaped radiation into two beams; rotating the intensity profile of one of the beams by 90 degrees with respect to the other; recombining the beams; and coupling the recombined beam into the one or more peripheral modes of the fiber. And in certain embodiments, coupling the depletion radiation into the one or more peripheral modes of the fiber includes shaping the radiation into a profile having an intensity minimum in a central portion thereof (e.g., in an appropriate Hermite-Gaussian mode such as 1.0 or 0.1), for example, using a spatial light modulator; separating the shaped radiation into two beams having orthogonal polarizations (e.g., using a polarization beam splitter); rotating the intensity profile of first one of the beams by about 90 degrees with respect to the other beam (e.g., with a Dove prism) and delaying the first one of the beams with respect to the other beam; recombining the beams (e.g., using a polarization beam splitter); and coupling the recombined beam into the one or more peripheral modes of the fiber. In certain desirable such embodiments, the shaped radiation has two lobes with an intensity minimum in the center.

As the person of ordinary skill in the art will appreciate, fluorescence excitation wavelengths will vary depending on the object to be imaged, and specifically on the particular species that is to undergo fluorescence. In certain embodiments, the excitation wavelength is 488 nm, or in the range of 400-600 nm. The excitation radiation can be pulsed, for example. In certain embodiments, the excitation wavelength is selected to provide two-photon absorbance in the object (i.e., is "two-photon radiation") to allow for two-photon microscopy. In certain such embodiments, the excitation wavelength is 900-1050 nm. The person of ordinary skill in the art will appreciate that excitation radiation will typically have a spread of wavelengths with a relative maximum at or near the fluorescence excitation wavelength.

Similarly, fluorescence depletion wavelengths will vary depending on the object to be imaged, and specifically on the particular species that is to undergo fluorescence. In certain embodiments, the fluorescence depletion wavelength is in the range of 500-700 nm, e.g., 585 nm. The fluorescence depletion wavelength is typically longer than the fluorescence excitation wavelength in the case of single-photon systems, or is no less than half of the fluorescence excitation wavelength in the case of two-photon systems. The fluorescence depletion radiation can be pulsed, for example. The person of ordinary skill in the art will appreciate that fluorescence depletion radiation will typically have a spread of wavelengths with a relative maximum at or near the fluorescence depletion wavelength.

As described above, the methods and systems described herein can be successfully operated even in cases where the polarization-maintaining optical fiber is bent. In certain embodiments as otherwise described herein, the polarization-maintaining optical fiber is disposed with one or more radii of curvature, and wherein the lowest radius of curvature is in the range of 20 mm to 250 mm, e.g., 20-200 mm, or 20-150 mm, or 20-100 mm, or 35-250 mm, or 35-200 mm, or 35-150 mm, or 35-100 mm, or 50-250 mm, or 50-200 mm, or 50-150 mm, or 50-100 mm.

The person of ordinary skill in the art, based on the disclosure herein, will select a length of the polarization-maintaining optical fiber that provides for convenient operation in a desired microscopy method or system. In certain embodiments of the methods and systems as otherwise described herein, the polarization-maintaining optical fiber has a length in the range of 200 cm to 10 m, e.g., in the range of 500 cm to 10 m, or in the range of 1 m to 10 m.

A variety of types of polarization-maintaining optical fibers can be used in the practice of the methods and systems of the disclosure. For example, fibers in which one or more stress rods are disposed in the optical fiber, e.g., in the so-called panda, bow-tie or elliptical-clad arrangements, can be used. In other embodiments, a fiber having shaped core having one axis substantially wider than an orthogonal axis can be used. However, in certain embodiments of the methods and systems as otherwise described herein, the polarization-maintaining optical fiber does not comprise a high-index ring core separated from a central core by a low-index region The excitation radiation and depletion radiation can be provided from the polarization-maintaining optical fiber to the object to be imaged in in a number of ways; the embodiments described above are merely examples. In certain embodiments as otherwise described herein, delivering the excitation radiation and the depletion radiation from the optical fiber to the object to be imaged includes collimating the output of the fiber and delivering the collimated output of the fiber to the object to be imaged. And in certain embodiments, delivering the excitation radiation and the depletion radiation from the optical fiber to the object to be imaged comprises collimating the output of the fiber; using one or more lenses to focus the collimated output onto a GRIN lens; and using the GRIN lens to conduct the radiation to the object. The GRIN lens can be, for example, detachable from the one or more lenses. The one or more lenses can, for example, include a pair of achromatic doublet lenses and a glass concave lens configured to balance the achromaticity of the GRIN lens.

The intensity of the emission radiation can be determined in in a number of ways; the embodiments described above are merely examples. In certain embodiments of the methods and systems as otherwise described herein, determining the intensity of the emission radiation includes propagating the emission radiation in the optical fiber in a direction opposite the propagation of the excitation and depletion radiation, and determining the intensity of the propagated emission radiation. In certain embodiments of the methods and systems as otherwise described herein, determining the intensity of the emission radiation comprises propagating the emission radiation in an optical fiber separate from the polarization-maintaining optical fiber.

The following listing of numbered embodiments form additional aspects of the disclosure. They may be combined and permuted in any fashion and in any number that is not logically or technically inconsistent.

Embodiment 1

A method for stimulated emission depletion microscopy of a fluorescent species in an object to be imaged, the fluorescent species having a fluorescence excitation wavelength, a fluorescence depletion wavelength and an fluorescence emission wavelength, the method comprising:
  providing a polarization-maintaining optical fiber;
  propagating excitation radiation of the fluorescence excitation wavelength in a central mode of the polarization-maintaining optical fiber;
  propagating depletion radiation of the fluorescence depletion wavelength in one or more peripheral modes of the polarization-maintaining optical fiber, each of the one or more peripheral modes having a minimum of intensity substantially overlapping the central mode of the polarization-maintaining optical fiber, the depletion radiation propagating substantially temporally incoherently in the polarization-maintaining optical fiber;
  delivering the excitation radiation and the depletion radiation from the polarization-maintaining optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the excitation radiation spot, and the depletion radiation prevents emission of radiation of the fluorescence emission wavelength in the region of the annular depletion radiation; and determining the intensity of the emission radiation.

Embodiment 2

The method of embodiment 1, wherein the central mode of the polarization-maintaining optical fiber has a maximum at the center thereof, e.g., as in is a substantially Gaussian mode of the polarization-maintaining optical fiber.

Embodiment 3

The method of embodiment 1 or embodiment 2, wherein the depletion radiation is propagated in two orthogonal modes of the polarization-maintaining optical fiber.

Embodiment 4

The method of any of embodiments 1-3, wherein the depletion radiation is propagated in the polarization-maintaining optical fiber with substantial orbital angular momentum.

Embodiment 5

The method of any of embodiments 1-4, wherein the depletion radiation is in the shape of a toroid.

Embodiment 6

The method of any of embodiments 1-5, wherein the depletion radiation is propagated in the polarization-maintaining optical fiber in a plurality of (e.g., two) peripheral modes, wherein the temporal incoherence ($\gamma$) between the modes is no more than 0.3, e.g., no more than 0.2, no more than 0.15, or no more than 0.1.

Embodiment 7

The method of any embodiments 1-6, wherein the depletion radiation (i.e., as propagating in the fiber and/or as delivered at the object) has a contrast (i.e., from maximum intensity to minimum intensity at the center) of at least 13 dB, e.g., at least 15 dB, or at least 17 dB.

Embodiment 8

The method of any of embodiments 1-7, wherein the depletion radiation and the excitation radiation overlap to provide an effective excitation spot at the object (i.e., having the ability to cause fluorescence of the object) that is substantially smaller than the diffraction limit for the optical system (e.g., a full-width at half-maximum of no more than 75%, e.g., no more than 50%, or no more than 30% of that of the diffraction limit).

Embodiment 9

The method of embodiment 8, wherein the effective excitation spot has a diameter of no more than 200 nm, e.g., no more than 150 nm or no more than 125 nm, or in the range of 10-200 nm, e.g., 10-150 nm, or 10-125 nm., or 50-200 nm, or 50-150 nm, or 50-125 nm, or 100-200 nm, or 100-200 nm.

Embodiment 10

The method of any of embodiments 1-9, wherein propagating excitation radiation of the fluorescence excitation wavelength in a central mode of the fiber comprises providing excitation radiation from a source of excitation radiation (e.g., a laser, or a filtered broadband source, or an amplified spontaneous emission source, or a laser diode) and coupling the excitation radiation into the central mode of the fiber (e.g., by focusing the excitation radiation onto a central portion of an endface of the optical fiber).

Embodiment 11

The method of any of embodiments 1-10, wherein the fluorescence excitation wavelength is in the range of 400-600 nm, e.g., 488 nm.

Embodiment 12

The method of any of embodiments 1-10, wherein the excitation radiation is two-photon radiation, and wherein the fluorescence excitation wavelength is in the range of 900-1050 nm.

Embodiment 13

The method of any of embodiments 1-12, wherein propagating depletion radiation of the fluorescence depletion wavelength comprises providing depletion radiation from a source of depletion radiation (e.g., a laser, or a filtered broadband source, or an amplified spontaneous emission source, or a laser diode) and coupling the depletion radiation into the one or more peripheral modes of the fiber (e.g., by focusing the depletion radiation onto a peripheral portion of an endface of the optical fiber).

Embodiment 14

The method of embodiment 13, wherein coupling the depletion radiation into the one or more peripheral modes of the fiber comprises
 shaping the radiation into a profile having an intensity minimum in a central portion thereof, (e.g., in an appropriate Hermite-Gaussian mode such as 1.0 or 0.1), for example, using a spatial light modulator;
 separating the shaped radiation into two beams;
 rotating the intensity profile of one of the beams by 90 degrees with respect to the other;
 recombining the beams; and
 coupling the recombined beam into the one or more peripheral modes of the fiber.

Embodiment 15

The method of embodiment 13, wherein coupling the depletion radiation into the one or more peripheral modes of the fiber comprises
 shaping the radiation into a profile having an intensity minimum in a central portion thereof (e.g., in an appropriate Hermite-Gaussian mode such as 1.0 or 0.1), for example, using a spatial light modulator;

separating the shaped radiation into two beams having orthogonal polarizations (e.g., using a polarization beam splitter);

rotating the intensity profile of first one of the beams by about 90 degrees with respect to the other beam (e.g., with a Dove prism) and delaying the first one of the beams with respect to the other beam;

recombining the beams (e.g., using a polarization beam splitter); and coupling the recombined beam into the one or more peripheral modes of the fiber.

Embodiment 16

The method of any of embodiments 14-15, wherein the shaped radiation has two lobes with an intensity minimum in the center.

Embodiment 17

The method of any of embodiments 1-16, wherein the peripheral modes of the polarization-maintaining optical fiber are Hermite-Gaussian modes (e.g., having at least one odd numbered identifier, such as 0.1; 1.0; 2.1; 1.2).

Embodiment 18

The method of any of embodiments 1-16, wherein polarization-maintaining the optical fiber is disposed with one or more radii of curvature, and wherein the lowest radius of curvature is in the range of 20 mm to 250 mm, e.g., 20-200 mm, or 20-150 mm, or 20-100 mm, or 35-250 mm, or 35-200 mm, or 35-150 mm, or 35-100 mm, or 50-250 mm, or 50-200 mm, or 50-150 mm, or 50-100 mm.

Embodiment 19

The method of any of embodiments 1-18, wherein the polarization-maintaining optical fiber has a length in the range of 200 cm to 10 m, e.g., in the range of 500 cm to 10 m, or in the range of 1 m to 10 m.

Embodiment 20

The method of any of embodiments 1-19, wherein the fluorescence depletion wavelength is in the range of 500-700 nm, e.g., 585 nm.

Embodiment 21

The method of any of embodiments 1-20, wherein delivering the excitation radiation and the depletion radiation from the optical fiber to the object to be imaged comprises collimating the output of the fiber and delivering the collimated output of the fiber to the object to be imaged.

Embodiment 22

The method of any of embodiments 1-20, wherein delivering the excitation radiation and the depletion radiation from the optical fiber to the object to be imaged comprises collimating the output of the fiber; using one or more lenses to focus the collimated output onto a GRIN lens; and using the GRIN lens to conduct the radiation to the object.

Embodiment 23

The method of embodiment 22, wherein the GRIN lens is detachable from the one or more lenses.

Embodiment 24

The method of embodiment 22 or embodiment 23, wherein the one or more lenses comprises a pair of achromatic doublet lenses and a glass concave lens configured to balance the achromaticity of the GRIN lens.

Embodiment 25

The method of any of embodiments 1-24, wherein the depletion radiation has a central dark portion having a −5 dB width at the object (i.e., as compared to the intensity maximum) that is in the range of 25 nm-300 nm in width, e.g., 25-200 nm, or 25-100 nm, or 50-300 nm, or 50-200 nm, 50-100 nm, or 75-300 nm, or 75-200 nm, or 100-300 nm, or 100-200 nm in width.

Embodiment 26

The method of embodiment 25, wherein the depletion radiation has a central dark portion having a −10 dB width at the object that is in the range of 10-150 nm in width, e.g., 10-125 nm, or 10-100 nm, or 10-75 nm, or 20-150 nm, or 20-125 nm, or 20-100 nm, or 20-75 nm, or 40-150 nm, or 40-125 nm, or 40-100 nm, or 40-75 nm in width.

Embodiment 27

The method of any of embodiments 1-26, wherein the intensity maximum of the excitation radiation at the object falls within a central dark portion of the depletion radiation at the object.

Embodiment 28

The method of any of embodiments 1-27, wherein determining the intensity of the emission radiation comprises propagating the emission radiation in the optical fiber in a direction opposite the propagation of the excitation and depletion radiation, and determining the intensity of the propagated emission radiation.

Embodiment 29

The method of any of embodiments 1-27, wherein determining the intensity of the emission radiation comprises propagating the emission radiation in an optical fiber separate from the polarization-maintaining optical fiber.

Embodiment 30

The method of any of embodiments 1-28, wherein the polarization-maintaining optical fiber does not comprise a high-index ring core separated from a central core by a low-index region.

Embodiment 31

An optical system configured to perform the method of any of claims 1-30.

Embodiment 32

The optical system of claim 31, comprising:
a polarization-maintaining optical fiber having a central mode and one or more peripheral modes each having a minimum of intensity substantially overlapping the central mode of the polarization-maintaining optical fiber;
a source of excitation radiation coupled to cause propagation of excitation radiation of the fluorescence excitation wavelength in the central mode of the polarization-maintaining optical fiber;
a source of depletion radiation of the depletion wavelength coupled to cause propagation of depletion radiation substantially temporally incoherently in one or more of the peripheral modes of the polarization-maintaining optical fiber;
the polarization-maintaining optical fiber being configured to deliver the excitation radiation and the depletion radiation from the optical fiber to the object to be imaged (e.g., optionally through additional optics), with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the spot, and the depletion radiation substantially prevents emission of radiation of the fluorescence emission wavelength in the region of the annular depletion radiation.

Embodiment 33

The system of embodiment 32, further comprising an intensity detector configured to determine the intensity of the emission radiation.

Embodiment 34

The system of embodiment 32 or embodiment 33, wherein the central mode of the polarization-maintaining optical fiber has a maximum at the center thereof, e.g., as in a substantially Gaussian mode of the polarization-maintaining optical fiber.

Embodiment 35

The system of any of embodiments 32-34, configured to propagate depletion radiation in two orthogonal modes of the polarization-maintaining optical fiber.

Embodiment 36

The system of any of embodiments 32-35, configured to propagate the depletion radiation in two orthogonal modes of the polarization-maintaining optical fiber.

Embodiment 37

The system of any of embodiments 32-36, configured to propagate the depletion radiation in the polarization-maintaining optical fiber with substantial orbital angular momentum.

Embodiment 38

The system of any of embodiments 32-37, configured to propagate the depletion radiation in the shape of a toroid.

Embodiment 39

The system of any of embodiments 32-38, wherein configured to propagate the depletion radiation in the polarization-maintaining optical fiber in a plurality of (e.g., two) peripheral modes, wherein the temporal incoherence ($\gamma$) between the modes being no more than 0.3, e.g., no more than 0.2, no more than 0.15, or no more than 0.1.

Embodiment 40

The system of any of embodiments 32-39, configured such that the depletion radiation (i.e., as propagating in the fiber and/or as delivered at the object) has a contrast (i.e., from maximum intensity to minimum intensity at the center) of at least 13 dB, e.g., at least 15 dB, or at least 17 dB.

Embodiment 41

The system of any of embodiments 32-40, wherein the depletion radiation and the excitation radiation overlap to provide an effective excitation spot at the object (i.e., having the ability to cause fluorescence of the object) that is substantially smaller than the diffraction limit for the optical system (e.g., a full-width at half-maximum of no more than 75%, no more than 50%, or no more than 30% of that of the diffraction limit).

Embodiment 42

The system of embodiment 41, wherein the effective excitation spot has a diameter of no more than 200 nm, e.g., no more than 150 nm or no more than 125 nm.

Embodiment 43

The system of any of embodiments 32-42, configured such that the excitation radiation is provided by a source of excitation radiation (e.g., a laser, or a filtered broadband source, or an amplified spontaneous emission source, or a laser diode) and coupled into the central mode of the fiber (e.g., by focusing the excitation radiation onto a central portion of an endface of the optical fiber).

Embodiment 44

The system of any of embodiments 32-43, wherein the fluorescence excitation wavelength is 488 nm. The person of ordinary skill in the art will appreciate that excitation radiation will typically have a spread of wavelengths with a relative maximum at or near the fluorescence excitation wavelength. The desired fluorescence excitation wavelength will depend on the particular species that is to undergo fluorescence. The excitation radiation can be pulsed.

Embodiment 45

The system of any of embodiments 32-43, wherein the excitation radiation is two-photon radiation, and wherein the fluorescence excitation wavelength is in the range of 900-1050 nm.

Embodiment 46

The system of any of embodiments 32-45, configured such that the depletion radiation of the fluorescence depletion wavelength is provided by a source of depletion radiation (e.g., a laser, or a filtered broadband source, or an amplified spontaneous emission source, or a laser diode) and coupled into the one or more peripheral modes of the fiber (e.g., by focusing the depletion radiation onto a peripheral portion of an endface of the optical fiber).

Embodiment 47

The system of embodiment 46, configured such that coupling the depletion radiation into the one or more peripheral modes of the fiber comprises
- shaping the radiation into a profile having an intensity minimum in a central portion thereof, (e.g., in an appropriate Hermite-Gaussian mode such as 1.0 or 0.1), for example, using a spatial light modulator;
- separating the shaped radiation into two beams;
- rotating the intensity profile of one of the beams by 90 degrees with respect to the other;
- recombining the beams; and
- coupling the recombined beam into the one or more peripheral modes of the fiber.

Embodiment 48

The system of embodiment 47, configured such that coupling the depletion radiation into the one or more peripheral modes of the fiber comprises
- shaping the radiation into a profile having an intensity minimum in a central portion thereof (e.g., in an appropriate Hermite-Gaussian mode such as 1.0 or 0.1), for example, using a spatial light modulator;
- separating the shaped radiation into two beams having orthogonal polarizations (e.g., using a polarization beam splitter);
- rotating the intensity profile of first one of the beams by about 90 degrees with respect to the other beam (e.g., with a Dove prism) and delaying the first one of the beams with respect to the other beam;
- recombining the beams (e.g., using a polarization beam splitter); and
- coupling the recombined beam into the one or more peripheral modes of the fiber.

Embodiment 49

The system of embodiment 47 or embodiment 48, configured such that the shaped radiation has two lobes with an intensity minimum in the center.

Embodiment 50

The system of any of embodiments 32-49, wherein the peripheral modes of the polarization-maintaining optical fiber are Hermite-Gaussian modes (e.g., having at least one odd numbered identifier, such as 0.1; 1.0; 2.1; 1.2).

Embodiment 51

The system of any of embodiments 32-50, wherein the optical fiber is disposed with one or more radii of curvature, and wherein the lowest radius of curvature is in the range of 20 mm to 250 mm, e.g., 20-200 mm, or 20-150 mm, or 20-100 mm, or 35-250 mm, or 35-200 mm, or 35-150 mm, or 35-100 mm, or 50-250 mm, or 50-200 mm, or 50-150 mm, or 50-100 mm.

Embodiment 52

The system of any of embodiments 32-51, wherein the polarization-maintaining optical fiber has a length in the range of 200 cm to 10 m, e.g., in the range of 500 cm to 10 m, or in the range of 1 m to 10 m.

Embodiment 53

The system of any of embodiments 32-52, wherein the fluorescence depletion wavelength is 585 nm. The person of ordinary skill in the art will appreciate that depletion radiation will typically have a spread of wavelengths with a relative maximum at or near the fluorescence depletion wavelength. The desired fluorescence depletion wavelength will depend on the particular species that is to undergo fluorescence. The depletion radiation can be pulsed.

Embodiment 54

The system of any of embodiments 32-53, configured such that delivering the excitation radiation and the depletion radiation from the optical fiber to the object to be imaged comprises collimating the output of the fiber and delivering the collimated output of the fiber to the object to be imaged.

Embodiment 55

The system of any of embodiments 32-53, configured such that delivering the excitation radiation and the depletion radiation from the optical fiber to the object to be imaged comprises collimating the output of the fiber; using one or more lenses to focus the collimated output onto a GRIN lens; and using the GRIN lens to conduct the radiation to the object.

Embodiment 56

The system of embodiment 55, wherein the GRIN lens is detachable from the one or more lenses.

Embodiment 57

The system of embodiment 55, wherein the one or more lenses comprises a pair of achromatic doublet lenses and a glass concave lens configured to balance the achromaticity of the GRIN lens.

Embodiment 58

The system of any of embodiments 1-57, configured such that the depletion radiation has a central dark portion having a −5 dB width at the object (i.e., as compared to the intensity maximum) that is in the range of 25 nm-300 nm in width, e.g., 25-200 nm, or 25-100 nm, or 50-300 nm, or 50-200 nm, 50-100 nm, or 75-300 nm, or 75-200 nm, or 100-300 nm, or 100-200 nm in width.

Embodiment 59

The system of embodiment 58, configured such that the depletion radiation has a central dark portion having a −10 dB width at the object that is in the range of 10-150 nm in width, e.g., 10-125 nm, or 10-100 nm, or 10-75 nm, or 20-150 nm, or 20-125 nm, or 20-100 nm, or 20-75 nm, or 40-150 nm, or 40-125 nm, or 40-100 nm, or 40-75 nm in width.

Embodiment 60

The system of any of embodiments 32-59, configured such that the intensity maximum of the excitation radiation at the object falls within a central dark portion of the depletion radiation at the object.

Embodiment 61

The system of any of embodiments 32-59, configured such that determining the intensity of the emission radiation comprises propagating the emission radiation in the optical fiber in a direction opposite the propagation of the excitation and depletion radiation, and determining the intensity of the propagated emission radiation.

Embodiment 62

The system of any of embodiments 32-59, configured such that determining the intensity of the emission radiation comprises propagating the emission radiation in an optical fiber separate from the polarization-maintaining optical fiber.

Embodiment 63

The system of any of embodiments 32-62, wherein the polarization-maintaining optical fiber does not comprise a high-index ring core separated from a central core by a low-index region.

It will be apparent to those skilled in the art that various modifications and variations can be made to the processes and devices described here without departing from the scope of the disclosure. Thus, it is intended that the present disclosure cover such modifications and variations of this invention provided they come within the scope of the appended claims and their equivalents.

What is claimed is:

1. A method for stimulated emission depletion microscopy of a fluorescent species in an object to be imaged, the fluorescent species having a fluorescence excitation wavelength, a fluorescence depletion wavelength and an fluorescence emission wavelength, the method comprising:
providing a polarization-maintaining optical fiber;
propagating excitation radiation of the fluorescence excitation wavelength in a central mode of the polarization-maintaining optical fiber;
propagating depletion radiation of the fluorescence depletion wavelength in one or more peripheral modes of the polarization-maintaining optical fiber, each of the one or more peripheral modes having a minimum of intensity substantially overlapping the central mode of the polarization-maintaining optical fiber, the depletion radiation propagating substantially temporally incoherently in the polarization-maintaining optical fiber;
delivering the excitation radiation and the depletion radiation from the polarization-maintaining optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the excitation radiation spot, and the depletion radiation prevents emission of radiation of the fluorescence emission wavelength in the region of the annular depletion radiation; and
determining the intensity of the emission radiation.

2. The method of claim 1, wherein the depletion radiation is propagated in two orthogonal modes of the polarization-maintaining optical fiber.

3. The method of claim 1, wherein the depletion radiation is in the shape of a toroid.

4. A method for stimulated emission depletion microscopy of a fluorescent species in an object to be imaged, the fluorescent species having a fluorescence excitation wavelength, a fluorescence depletion wavelength and an fluorescence emission wavelength, the method comprising:
providing a polarization-maintaining optical fiber;
propagating excitation radiation of the fluorescence excitation wavelength in a central mode of the polarization-maintaining optical fiber;
propagating depletion radiation of the fluorescence depletion wavelength in one or more peripheral modes of the polarization-maintaining optical fiber wherein the temporal incoherence ($\gamma$) between the modes is no more than 0.2, each of the one or more peripheral modes having a minimum of intensity substantially overlapping the central mode of the polarization-maintaining optical fiber, the depletion radiation propagating substantially temporally incoherently in the polarization-maintaining optical fiber;
delivering the excitation radiation and the depletion radiation from the polarization-maintaining optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the excitation radiation spot, and the depletion radiation prevents emission of radiation of the fluorescence emission wavelength in the region of the annular depletion radiation; and
determining the intensity of the emission radiation.

5. The method of claim 1, wherein the depletion radiation, as propagating in the fiber and/or as delivered at the object has a contrast, from maximum intensity to minimum intensity at the center of at least 13 dB.

6. The method of claim 1, wherein the depletion radiation and the excitation radiation overlap to provide an effective excitation spot at the object, having the ability to cause fluorescence of the object that is substantially smaller than the diffraction limit for the optical system.

7. The method of claim 6, wherein the effective excitation spot has a diameter of no more than 200 nm.

8. The method of claim 1, wherein the fluorescence excitation wavelength is in the range of 400-600 nm or in the range of 900-1050 nm, and the fluorescence depletion wavelength is in the range of 500-700 nm.

9. The method of claim 1, wherein propagating depletion radiation of the fluorescence depletion wavelength comprises providing depletion radiation from a source of depletion and coupling the depletion radiation into the one or more peripheral modes of the fiber, and wherein coupling the depletion radiation into the one or more peripheral modes of the fiber comprises
   shaping the radiation into a profile having an intensity minimum in a central portion thereof;
   separating the shaped radiation into two beams having orthogonal polarizations;
   rotating the intensity profile of first one of the beams by about 90 degrees with respect to the other beam and delaying the first one of the beams with respect to the other beam;
   recombining the beams; and
   coupling the recombined beam into the one or more peripheral modes of the fiber.

10. The method of claim 1, wherein the peripheral modes of the polarization-maintaining optical fiber in which depletion radiation of the fluorescence depletion wavelength is propagated are Hermite-Gaussian modes.

11. The method of claim 1, wherein delivering the excitation radiation and the depletion radiation from the optical fiber to the object to be imaged comprises collimating the output of the fiber and delivering the collimated output of the fiber to the object to be imaged.

12. The method of claim 1, wherein delivering the excitation radiation and the depletion radiation from the optical fiber to the object to be imaged comprises collimating the output of the fiber; using one or more lenses to focus the collimated output onto a GRIN lens; and using the GRIN lens to conduct the radiation to the object.

13. The method of claim 12, wherein the depletion radiation has a central dark portion having a −10 dB width at the object that is in the range of 10-150 nm in width.

14. The method of claim 1, wherein the intensity maximum of the excitation radiation at the object falls within a central dark portion of the depletion radiation at the object.

15. An optical system configured to perform the method of claim 1, the optical system comprising:
   a polarization-maintaining optical fiber having a central mode and one or more peripheral modes each having a minimum of intensity substantially overlapping the central mode of the polarization-maintaining optical fiber;
   a source of excitation radiation coupled to cause propagation of excitation radiation of the fluorescence excitation wavelength in the central mode of the polarization-maintaining optical fiber;
   a source of depletion radiation of the depletion wavelength coupled to cause propagation of depletion radiation substantially temporally incoherently in one or more of the peripheral modes of the polarization-maintaining optical fiber;
   the polarization-maintaining optical fiber being configured to deliver the excitation radiation and the depletion radiation from the optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the spot, and the depletion radiation substantially prevents emission of radiation of the fluorescence emission wavelength in the region of the annular depletion radiation.

16. The method of claim 10, wherein at least one of the Hermite-Gaussian modes has at least one odd-numbered identifier.

17. A method for stimulated emission depletion microscopy of a fluorescent species in an object to be imaged, the fluorescent species having a fluorescence excitation wavelength, a fluorescence depletion wavelength and an fluorescence emission wavelength, the method comprising:
   providing a polarization-maintaining optical fiber;
   propagating excitation radiation of the fluorescence excitation wavelength in a central mode of the polarization-maintaining optical fiber;
   propagating depletion radiation of the fluorescence depletion wavelength in one or more peripheral modes of the polarization-maintaining optical fiber, each of the one or more peripheral modes being a Hermite-Gaussian mode having a minimum of intensity substantially overlapping the central mode of the polarization-maintaining optical fiber, the one or more modes including a 1.0 Hermite-Gaussian mode or a 0.1 Hermite-Gaussian mode the depletion radiation propagating substantially temporally incoherently in the polarization-maintaining optical fiber;
   delivering the excitation radiation and the depletion radiation from the polarization-maintaining optical fiber to the object to be imaged, with the excitation radiation forming a spot having a substantially centrally-disposed intensity maximum and depletion radiation forming an annular ring about the excitation radiation and substantially overlapping the periphery of the excitation radiation spot without substantially overlapping the centrally-disposed intensity maximum of the excitation radiation spot, wherein the excitation radiation causes emission radiation of the fluorescence emission wavelength from the object at the centrally-disposed intensity maximum of the excitation radiation spot, and the depletion radiation prevents emission of radiation of the fluorescence emission wavelength in the region of the annular depletion radiation; and
   determining the intensity of the emission radiation.

18. The method of claim 4, wherein the depletion radiation is propagated in two orthogonal modes of the polarization-maintaining optical fiber.

19. The method of claim 4, wherein the depletion radiation, as propagating in the fiber and/or as delivered at the object has a contrast, from maximum intensity to minimum intensity at the center of at least 13 dB.

20. The method of claim 4, wherein the depletion radiation and the excitation radiation overlap to provide an effective excitation spot at the object, having the ability to cause fluorescence of the object that is substantially smaller than the diffraction limit for the optical system.

* * * * *